US008148123B2

(12) United States Patent
Hartman et al.

(10) Patent No.: US 8,148,123 B2
(45) Date of Patent: Apr. 3, 2012

(54) METHODS FOR LOWERING ELEVATED URIC ACID LEVELS USING INTRAVENOUS INJECTIONS OF PEG-URICASE

(75) Inventors: Jacob Hartman, Holon (IL); Simona Mendelovitz, Ramat Aviv, IL (US); Claudia D. Rehrig, Plainsboro, NJ (US); William Huang, Florham Park, NJ (US); Michael Hershfield, Durham, NC (US)

(73) Assignee: Savient Pharmaceuticals, Inc., East Brunswick, NJ (US)

( * ) Notice: Subject to any disclaimer, the term of this patent is extended or adjusted under 35 U.S.C. 154(b) by 515 days.

(21) Appl. No.: 11/539,475

(22) Filed: Oct. 6, 2006

(65) Prior Publication Data
US 2007/0274977 A1  Nov. 29, 2007

Related U.S. Application Data

(63) Continuation-in-part of application No. PCT/US2006/013660, filed on Apr. 11, 2006, and a continuation-in-part of application No. PCT/US2006/013502, filed on Apr. 11, 2006.

(60) Provisional application No. 60/670,541, filed on Apr. 11, 2005, provisional application No. 60/670,573, filed on Apr. 11, 2005.

(51) Int. Cl.
*C12N 9/02* (2006.01)
*C12N 11/06* (2006.01)

(52) U.S. Cl. ........................................ 435/189; 435/181

(58) Field of Classification Search ................ 424/94.1, 424/94.4; 435/181, 189
See application file for complete search history.

(56) References Cited

U.S. PATENT DOCUMENTS

| | | |
|---|---|---|
| 3,451,996 A | 6/1969 | Sumyk et al. |
| 3,616,231 A | 10/1971 | Bergmeyer et al. |
| 3,931,399 A | 1/1976 | Bohn et al. |
| 4,141,973 A | 2/1979 | Balazs |
| 4,169,764 A | 10/1979 | Takezawa et al. |
| 4,179,337 A | 12/1979 | Davis et al. |
| 4,297,344 A | 10/1981 | Schwinn et al. |
| 4,301,153 A | 11/1981 | Rosenberg |
| 4,312,979 A | 1/1982 | Takemoto et al. |
| 4,317,878 A | 3/1982 | Nakanishi et al. |
| 4,421,650 A | 12/1983 | Nagasawa et al. |
| 4,425,431 A | 1/1984 | Takemoto et al. |
| 4,460,575 A | 7/1984 | d'Hinterland et al. |
| 4,460,683 A | 7/1984 | Gloger et al. |
| 4,485,176 A | 11/1984 | Bollin, Jr. et al. |
| 4,753,796 A | 6/1988 | Moreno et al. |
| 4,766,106 A | 8/1988 | Katre et al. |
| 4,797,474 A | 1/1989 | Patroni et al. |
| 4,847,325 A | 7/1989 | Shadle et al. |
| 4,917,888 A | 4/1990 | Katre et al. |
| 4,945,086 A | 7/1990 | Benitz et al. |
| 4,966,963 A | 10/1990 | Patroni |
| 4,987,076 A | 1/1991 | Takashio et al. |
| 4,992,531 A | 2/1991 | Patroni et al. |
| 5,008,377 A | 4/1991 | Patroni et al. |
| 5,010,183 A | 4/1991 | Macfarlane |
| 5,283,317 A | 2/1994 | Saifer et al. |
| 5,286,637 A | 2/1994 | Veronese et al. |
| 5,362,641 A | 11/1994 | Fuks et al. |
| 5,382,518 A | 1/1995 | Caput et al. |
| 5,428,128 A | 6/1995 | Mensi-Fattohi et al. |
| 5,458,135 A | 10/1995 | Patton et al. |
| 5,468,478 A | 11/1995 | Saifer et al. |
| 5,529,915 A | 6/1996 | Phillips et al. |
| 5,541,098 A | 7/1996 | Caput et al. |
| 5,567,422 A | 10/1996 | Greenwald |
| 5,612,460 A | 3/1997 | Zalipsky et al. |
| 5,624,903 A | 4/1997 | Muller et al. |
| 5,633,227 A | 5/1997 | Muller et al. |
| 5,637,749 A | 6/1997 | Greenwald et al. |
| 5,643,575 A | 7/1997 | Martinez et al. |
| 5,653,974 A | 8/1997 | Hung et al. |
| 5,766,897 A | 6/1998 | Braxton |
| 5,811,096 A | 9/1998 | Aleman et al. |
| 5,880,255 A | 3/1999 | Delgado et al. |
| 5,919,455 A | 7/1999 | Greenwald et al. |
| 5,929,231 A | 7/1999 | Malkki et al. |
| 5,932,462 A | 8/1999 | Harris et al. |
| 5,948,668 A | 9/1999 | Hartman et al. |
| 5,955,336 A | 9/1999 | Shigyo et al. |

(Continued)

FOREIGN PATENT DOCUMENTS

| | | |
|---|---|---|
| DE | 279 486 A1 | 6/1990 |
| EP | 055188 | 1/1991 |
| EP | 0408461 A1 | 1/1991 |
| EP | 1 100 542 | 5/2001 |
| JP | 55-99189 | 7/1980 |
| JP | 62-55079 | 3/1987 |
| JP | 03-148298 | 6/1991 |
| JP | 09-154581 | 6/1997 |
| KR | 318706 | 12/2001 |
| KR | 10-0369838 | 1/2003 |

(Continued)

OTHER PUBLICATIONS

Abuchowski, A., et al. "Effect of Covalent Attachment of Polyethylene Glycol on Immunogenicity and Cirulating Life of Bovine Liver Catalase." J. Biol. Chem. 252-:3582-3586, American Society for Biochemistry and Molecular Biology (1977).

Abuchowski, A., et al., "Reduction of Plasma Urate Levels in the Cockerel with Polyethylene Glycol-Uricase," J. Pharmacol. Exp. Ther. 219:352-354, The American Society for Pharmacology and Experimental Therapeutics (1981).

Alvares, K., et al., "The Nucleotide Sequence of a Full Length cDNA Clone Encoding Rat Liver Urate Oxidase," Biochem. Biophys. Res. Commun. 158:991-995, Academic Press, Inc. (1989).

(Continued)

*Primary Examiner* — Ruth Davis
(74) *Attorney, Agent, or Firm* — Kramer Levin Naftalis & Frankel LLP

(57) ABSTRACT

A method for lowering elevated uric acid levels in patients is disclosed and consists of administering to the patients an intravenous injection of PEG-uricase having a dosage from about 4 to about 12 mg.

18 Claims, 5 Drawing Sheets

U.S. PATENT DOCUMENTS

| | | | |
|---|---|---|---|
| 6,201,110 B1 | 3/2001 | Olsen et al. | |
| 6,211,341 B1 | 4/2001 | Zeelon et al. | |
| 6,201,110 B1 | 3/2001 | Olsen et al. | |
| 6,211,341 B1 | 4/2001 | Zeelon et al. | |
| 6,468,210 B1 | 10/2002 | Iliff | |
| 6,475,143 B2 | 11/2002 | Iliff | |
| 6,524,241 B2 | 2/2003 | Iliff | |
| 6,527,713 B2 | 3/2003 | Iliff | |
| 6,569,093 B2 | 5/2003 | Iliff | |
| 6,576,235 B1 * | 6/2003 | Williams et al. | 424/94.4 |
| 6,608,892 B2 | 8/2003 | Shaffer et al. | |
| 6,783,965 B1 | 8/2004 | Sherman et al. | |
| 6,913,915 B2 | 7/2005 | Ensor et al. | |
| 2002/0010319 A1 | 1/2002 | Ansaldi et al. | |
| 2003/0082786 A1 | 5/2003 | Ensor et al. | |
| 2003/0166249 A1 | 9/2003 | Williams et al. | |
| 2005/0014240 A1 | 1/2005 | Sherman et al. | |
| 2008/0159976 A1 | 7/2008 | Hartman et al. | |
| 2009/0169534 A1 | 7/2009 | Hartman et al. | |
| 2009/0209021 A1 | 8/2009 | Hartman et al. | |
| 2009/0317889 A1 | 12/2009 | Fischer et al. | |

FOREIGN PATENT DOCUMENTS

| | | |
|---|---|---|
| WO | WO8604145 A1 | 7/1986 |
| WO | 333148 | 9/1994 |
| WO | WO 94/19007 A1 | 9/1994 |
| WO | WO 94/23735 | 10/1994 |
| WO | WO9511987 A1 | 5/1995 |
| WO | WO 96/23064 | 8/1996 |
| WO | 365606 | 3/1998 |
| WO | WO 98/31383 A1 | 7/1998 |
| WO | 488848 | 2/2000 |
| WO | WO 00/07629 A2 | 2/2000 |
| WO | WO 00/08196 A3 | 2/2000 |
| WO | WO 01/59078 A2 | 8/2001 |
| WO | WO03045436 A1 | 6/2003 |

OTHER PUBLICATIONS

Alvares, K., et al., "Rat urate oxidase produced by recombinant baculovirus expression: Formation of peroxiscome crystallized core-like structures," Proc. Natl. Acad. Sci. USA 89:4908-4912, National Academy of Sciences (1992).

Braun, A. And Alsenz, J., "Development and Use of Enzyme-Linked Immunosorbent Assays (ELISA) for the Detection of Protein Aggregates in Interferon-Alpha (IFN-α) Formulations," Pharm. Res. 14:1394-1400, Plenum Publishing Corporation (Oct. 1997).

Braun, A., et al. "Protein Aggregates Seem to Play a Key Role Among the Parameters Influencing the Antigenicity of Interferon Alpha (IFN-α) in Normal and Transgenic Mice," Pharm. Res. 14:1472-1478, Plenum Publishing Corporation (Oct. 1997).

Burnham, N.L., "Polymers for delivering peptides and proteins," Am. J. Hosp. Pharm. 51:210-218, American Society of Hospital Pharmacists, Inc. (1994).

Caliceti, P., et al., "Biopharmaceutical Properties of Uricase Conjugated to Neutral and Amphiphilic Polymers," Bioconjugate Chem. 10:639-646, American Chemical Society (Jul.-Aug. 1999).

Chen, R.H.-L., et al., "Properties of Two Urate Oxidases Modified by the Covalent Attachment of Poly(Ethylene Glycol)," Biochem. Biophys. Acta 660:293-298, Elsevier/North Holland Biomedical Press (1981).

Chua, C.C., et al., "Use of Polyethylene Glycol-Modified Uricase (PEG-Uricase) to Treat Hyperuricemia in a Patient with Non-Hodgkin Lymphoma," Ann. Intern. Med. 109:114-117, American College of Physicians (1988).

Colloc'h, N., et al., "Crystal Structure of the protein drug urate oxidase-inhibitor complex at 2.05 A resolution," Nature Struct. Biol. 4:947-952, Nature Publishing Company (Nov. 1997).

Conley, T.G., and Priest, D.G., "Thermodynamics and Stoicheiometry of the Binding of Substrate Analogues to Uricase," Biochem. J. 187:727-732, The Biochemical Society (1980).

Davis, F.F., et al., "Enzyme-Polyethylene Glycol Adducts: Modified Enzymes with Unique Properties," in: Enzyme Engineering, vol. 4, Braun, G.B., et al., eds., Plenum Press, New York, pp. 169-173 (1978).

Davis, S., et al., "Hypouricaemic Effect of Polyethyleneglycol Modified Urate Oxidase," Lancet 2:281-283, Lancet Publishing Group (1981).

Donadio, D., et al., "Manifestation de type anaphylactique après injection intra-veineuse d'urate-oxydase chez un enfant asthmatique atteint de leucèmie aiguë," La Nouv. Presse Med. 10:711-712, Masson (1981).

Unverified English language partial translation of Donadio, D., et al., "Anaphylaxis-like manifestations after intravenous injection of urate oxidase in an asthmatic child with acute leukemia," La Nouv. Presse Med. 10:711-712, Masson (1981) (Document NPL15).

Fam, A.G., "Strategies and Controversies in the Treatment of Gout and Hyperuricaemia," Ballière's Clinical Rheumatology 4:177-192, Ballière Tindall (1990).

Fridovich, I., "The Competitive Inhibition of Uricase by Oxonate and by Related Derivatives of s-Triazines," J. Biol. Chem. 240:2491-2494, American Society for Biochemistry and Molecular Biology (1965).

Fuertges, F., and Abuchowski, A., "The Clinical Efficacy of Poly(Ethylene Glycol)-Modified Proteins," J. Control. Release 11:139-148, Elsevier Science (1990).

Fujita, T., et al., "Tissue Distribution of 111 In-Labeled Uricase Conjugated with Charged Dextrans and Polyethylene Glycol," J. Pharmacobio-Dyn. 14:623-629, Pharmaceutical Society of Japan (1991).

Greenberg, M.L. and Hershfield, M.S., "A Radiochemcial-High-Performance Liquid Chromatographic Assay for Urate Oxidase in Human Plasma," Anal. Biochem. 176:290-293, Academic Press, Inc. (1989).

Hande, K.R., et al., "Severe Allpurinol Toxicity. Description and Guidelines for Prevention in Patients with Renal Insufficiency," Am. J. Med. 76:47-56, Excerpta Medica (1984).

Hedlund, L.W., et al., "Magnetic Resonance Microscopy of Toxic Renal Injury Induced by Bromoethylamine in Rats," Fundam. Appl. Toxicol. 16:787-797, Academic Press (1991).

Henney, C.S. and Ellis, E.F., "Antibody Production to Aggregated Human γG-Globulin in Acquired Hypogammaglobulinemia," New Engl. J. Med. 278:1144-1146, Massachusetts Medical Society (1968).

Herbst, R., et al., "Folding of Firefly (*Photinus pyralis*) Luciferase: Aggregation and Reactivation of Unfolding Intermediates," Biochem. 37:6586-6597, American Chemical Society (May 1998).

Hershfield, M.S., et al., "Use of Site-Directed Mutagenesis to Enhance the Epitope-shielding Effect of Covalent Modification of Proteins with Polyethylene Glycol," Proc. Natl. Acad. Sci. USA 88:7185-7189, Natinal Academy of Sciences (1991).

Hershfield, M.S., "Biochemistry and Immunology of Poly(ethylene glycol)-Modified Adenosine Deaminase (PEG-ADA)," in: ACS Symposium Series 680. Poly(ethylene glycol). Chemistry and Biological Applications, Harris, J.M. and Zalipsky, S., eds., American Chemical Society, Washington, DC. pp. 145-154 (first available.

Ishino, K. and Kudo, S., "Proteins Concentration Dependence on Aggregation Behavior and Properties of Soybean 7S and 11S Globulins during Alkali-treatment," Agric. Biol. Chem. 44:1259-1266, Agricultural Chemical Society of Japan (1980).

Ito, M., et al., "Identification of an Amino Acid Residue Involved in the Substrate-binding Site of Rat Liver Uricase by Site-directed Mutagenesis," Biochem. Biophys. Res. Commun. 187:101-107, Academic Press (1992).

Kahn, K., and Tipton, P.A., "Kinetic Mechanism and Cofactor Content of Soybean Root Nodule Rate Oxidase," Biochemistry 36:4731-4738, American Chemical Society (Apr. 1997).

Kelly, S.J., et al., "Diabetes Insipidus in Uricase-Deficient Mice: A Model for Evaluating Therapy with Poly (Ethylene Glycol)-Modified Uricase," J. Am. Soc. Nephrol. 12:1001-1009, Lippincott Williams & Wilkins (May 2001).

Kito, M., et al. "A Simple and Efficient Method for Preparation of Monomethoxpolyethylene Glycol Activated with p-Nitrophenylchloroformate and Its Application to Modification of L-Asparaginase," J. Clin. Biochem. Nutr. 21:101-111, Institute of Applied Biochemistry (1996).

Kunitani, M., et al., "On-line characterization of polyethylene glycol-modified proteins," J. Chromat. 588:125-137, Elsevier Science Publishers B.V. (1991).
Kunitani, M., et al., "Classical light scattering quantitation of protein aggregates: off-line spectroscopy versus HPLC detection," J. Pharm. Biomed. Anal. 16:573-586, Elsevier Science B.V. (Dec. 1997).
Leach, M., et al., "Efficacy of Urate Oxidase (Uricozyme) in Tumour Lysis Induced Urate Nephropathy," Clin. Lab. Haematol. 20:169-172, Blackwell Scientific Publications (Jun. 1998).
Lee, C.C., et al., "Generation of cDNA Probes Directed by Amino Acid Sequence: Cloning of Urate Oxidase," Science 239:1288-1291, American Association for the Advancement of Science (1988).
Legoux, R. et al., "Cloning and Expression in *Escherichia coli* of the Gene Encoding *Aspergillus flavus* Urate Oxidase," J. Biol. Chem. 267:8565-8570, American Society for Biochemistry and Molecular Biology (1992).
Mahmoud, H.H., et al., "Advances in the Management of Malignancy-Associated Hyperuricaemia," Br. J. Cancer (Supplement 4)77:18-20, Churchill Livingstone (Jun. 1998).
Mahler, H.R., et al., "Studies of Uricase, I. Preparation, Purification, and Properties of a Cuproprotein," J. Biol. Chem. 216:625-641, American Society for Biochemistry and Molecular Biology (1955).
Malakhova, E.A., et al., "Kinetic Properties of Bacterial Urate Oxidase Entrapped in Hydrated Reversed Micelles," Biologicheskie Membrany 8:453-459, Nauka (1991).
Mirua, S., et al., "Urate Oxidase in Imported into Peroxisomes Recognizing the C-terminal SKL Motif of Proteins," Eur. J. Biochem. 223:141-146, Blackwell Science Ltd. (1994).
Monkarsh, S.P., et al., "Positional Isomers of Monopegylated Interferon $\alpha$-2a: Isolation, Characterization, and Biological Activity ," Analytical Biochemistry 247:434-440, Academic Press (1997).
Montalbini, P., et al., "Uricase form leaves: its purification and characterization from three different higher plants," Planta 202:277-283, Springer-Verlag (Jun. 1997).
Moore, W.V. and Leppert, P., "Role of Aggregated Human Growth Hormone (hGH) in Development of Antibodies to hGH," J. Clin. Endocrinol. Metab. 51:691-697, The Endocrine Society (1980).
Nishida, Y., et al., "Hypouricaemic effect after oral administration in chickens of polyethylene glycol-modified uricase entrapped in liposomes," J. Pharm. Pharmacol. 36:354-355, Pharmaceutical Press (1984).
Nishimura, H., et al., "Modification of Yeast Uricase with Polyethlene Glycol: Disappearance of Binding Ability towards Anti-Uricase Serum," Enzyme 24:261-264, Karger (1979).
Nishimura, H., et al., "Improved Modification of Yeast Uricase with Polyethylene Glycol, Accompanied with Nonimmunoreactivity Towards Anti-Uricase Serum and High Enzymic Activity," Enzyme 26:49-53, Karger (1981).
Nucci, M.L., et al., "The Therapeutic Value of Poly(Ethylene Glycol)-Modified Proteins," Adv. Drug Deliv. Rev. 6:133-151, Elsevier Science Publishers (1991).
Osman, A.M., et al., "Liver Uricase in *Camelus dromedarius*: Purification and Properties," Comp. Biochem. Physiol. 94B:469-474, Pergamon Press Plc. (1989).
Palleroni, A.V., et al., "Interferon Immunogenicity: Preclinical Evaluation of Interferon-$\alpha$2a," J. Interferon Cyto. Res. 17:S23-S27, Mary Ann Liebert, Inc. (Jul. 1997).
"PEG-Uricase BioTechnology General, Duke University, Mountain View licensing agreement," R&D Focus Drug News, Accession No. 1998-2984, available on Datastar File IPNR/IPNA, (Aug. 1998).
Porstmann, B., et al., "Comparision of Chromogens for the Determination of Horseradish Peroxidase as a Marker in Enzyme Immunoassay," J. Clin. Chem. Clin. Biochem. 19:435-439, Walter de Gruyter & Co. (1981).
Pui, C-H., et al., "Urate oxidase in prevention and treatment of hyperuricemia associated with lymphoid malignancies," Leukemia 11:1813-1816, Stockton Press (Nov. 1997).
Saifer, M.G.P., et al., "Plasma Clearance and Immunologic Properties of Long-Acting Superoxide Dismutase Prepared Using 35,000 to 120,000 Dalton Poly-Ethylene Glycol," in: Free Radicals in Diagnostic Medicine, Armstrong, D., ed., Plenum Press, New York, NY, pp. 377-387 (1994).

Saifer, M.G.P., et al., "Improved Conjugation of Cytokines Using High Molecular Weight Poly(ethylene glycol): PEG-GM-CSF as a Prototype," Polymer Prepr. 38:576-577, American Chemical Society (Apr. 1997).
Sartore, L., et al., "Enzyme Modification by MPEG with an Amino Acid or Peptide as Spacer Arms," Appl. Biochem. Biotechnol. 27:45-54, Humana Press (1991).
Savoca, K.V., et al., "Induction of Tolerance in Mice by Uricase and Monomethoxypolyethylene Glycol-Modified Uricase," Int. Archs. Allergy appl. Immun. 75:58-67, Karger (1984).
Shearwater Polymers Inc., "Functionalized biocompatible Polymers for Research and Pharmaceuticals," in: Shearwater Polymers, Inc., Catalog, pp. 27, 47, and 48. (Jul. 1997).
Sherman, M.R., et al., "Conjugation of High-Molecular Weight Poly(ethyleneglycol) to Cytokines: Granulocyte-Macrophage Colony-Stimulating Factors as Model Substrates," in:ACS Symposium Series 680. Poly(ethylene glycol). Chemistry and Biological Applications, Hanis, J.M. and Zalipsky. S., eds., American Chemical Society, Washington, DC, pp. 155-169 (Apr. 1997).
Somack, R., et al., "Preparation of Long-Acting Superoxide Dismutase Using High Molecular Weight Polyethylene Glycol (41,000-72,000 Daltons)," Free Rad. Res. Comms. 12-13:553-562, Harwood Academic Publishers GmbH (1991).
Suzuki, H. and Verma, D.P.S., "Soybean Nodule-Specific Uricase (Nodulin-35) Is Expressed and Assembled into a Functional Tetrameric Holoenzyme in *Escherichia coli*," Plant Physiol. 95:384-389, American Society of Plant Physiologists (1991).
Treuheit, M.J., et al., "Inverse Relationship of Protein Concentration and Aggregation," Pharm. Res. 19:511-516, Plenum Publishing Corporation (Apr. 2002).
Tsuji, J.-I., et al., "Studies on Antigenicity of the Polyethylene Glycol (PEG)-Modified Uriacse," Int. J. Immunopharmacol. 7:725-730, Elsevier Science (1985).
Venkataseshan, V.S., et al., "Acute Hyperuricemic Nephropathy and Renal Failure after Transplantation," Nephron 56:317-321, Karger AG (1990).
Veronese, F.M., et al., "Surface Modification of Proteins. Activation of Monomethoxy-Polyethylene Glycols by Phenylchloroformates and Modification of Ribonuclease and Superoxide Dismutase," Appl. Biochem. Biotechnol. 11:141-152, The Humana Press, Inc. (1985).
Veronese, F.M., et al., "New Synthetic Polymers for Enzyme and Liposome Modification," in: ACS Symposium Series 680, Poly(Ethylene Glycol) Chemistry and Biological Applications, Harris, J.M., and Zalipsky, S., eds., American Chemical Society, Washington, D.C. pp. 182-192 (Apr. 1997).
Wallrath, L.L., et al., "Molecular Characterization of the *Drosophila melanogaster* Urate Oxidase Gene, an Ecdysone-Repressible Gene Expressed Only in the Malpighian Tubules," Molec. Cell. Biol. 10:5114-5127, American Society for Microbiology (1990).
Wang, X., et al., "Rat urate oxidase: cloning and structural analysis of the gene and 5'-flanking region," Gene 97:223-229, Elsevier Science Publishers B.V. (1991).
Wu, X., et al., "Urate oxidase: Primary structure and evolutionary implications," Proc. Natl. Acad. Sci. USA 86:9412-9416, National Academy of Sciences (1989).
Wu, X., et al., "Two Independent Mutational Events in the Loss of Urate Oxidase during Hominoid Evolution," J. Mol. Evol. 34:78-84, Springer-Verlag (1992).
Wu, X., et al., "Hyperuricemia and urate nephropathy in urate oxidase-deficient mice," Proc. Natl. Acad. Sci. USA 91:742-746, National Academy of Sciences (1994).
Yasuda, Y., et al., "Biochemcial and Biopharmaceutical Properties of Macromolecular Conjugates of Uricase with Dextran Polyethylene Glycol," Chem. Pharm. Bull. 38:2053-2046, Pharmaceutical Society of Japan (1990).
Yeldandi, A.V., et al., "Human Urate Oxidase Gene: Cloning and Partial Sequence Analysis Reveal a Stop Codon within the Fifth Exon," Biochem. Biophys. Res. Commun. 171:641-646, Academic Press (1990).
U.S. Trademark Registration No. 2,246,623, entitled "Puricase," filed Jul. 15, 1997.
Dialog file 351, Accession No. 8448552, Unverified WPI English language abstract for DD 279486 (Document FP3).

"E.C. 1.7.3.3., urate oxidase," BRENDA Enzyme Database, available via internet at www.brenda.uni-koeln.de/.
Esp@cenet database, Unverified English language abstract for JP 09-154581 (Document FP6).
NCBI Entrez, GenBank Report, Accession No. NP_446220, Wang, X.D., et al. (Oct. 2004).
Patent Abstracts of Japan, Unverified English language abstract for JP-55-099189 (Document FPI).
Patent Abstracts of Japan, Unverified English language abstract for JP 62-055079 (Document FP2).
Patent Abstracts of Japan, Unverified English language abstract for JP 03-148298 (Document FP4).
S. Sundy et al., Arthritis & Rheumatism, vol. 52, No. 9 (Supplement), Sep. 2005, Abstract Supplement, 2005 annual Scientific Meeting, Nov. 12-17, 2005, San Diego, Califomia; 1836.
Michael A. Becker, Hyperuricemia and Gout, In: The Metabolic and Molecular Bases of Inherited Disease. Edited by Scriver CR, Beaudet AL, Sly WS, Valle D, 8th edn. New York; McGraw-Hill; 2001: 2513-2535.
Terkeltaub RA: Clinical practice. Gout. N. Engl. J. Med. 2003, 349(17): 1647-1655.
Wortmann RL et al.: Gout and Hyperuricemia. In: Kelley's Textbook of Rheumatology. Edited by Ruddy S, Harris Ed, Jr., Sledge CB, 6th edn. St. Louis: W.B. Saunders: 2001: 1339-1371.
Li-Yu J et al., Treatment of Chronic Gout.. Can We Determine When Urate Stores Are Depleted Enough to Prevent Attacks of Gout?, J. Rheumatol 2001, 28(3):577-580.
Perez-Ruiz F. et al., Effect of Urate-Lowering Therapy on the Velocity of Size Reduction of Tophi in Chronic Gout, Arthritis Rheum. 2002, 47(4); 356-360.
Shoji A. et al., A Retrospective Study of the Relationship Between Serum Urate Level and Recurrent Attacks of Gouty Arthritis: Evidence for Reduction of Recurrent Gouty Arthritis With Antihyperuricemic Therapy, ; arthritis Rheum. 2004, 51(3):321-325.
Coiffier B. et al., Efficacy and Safety of Rasburicase (recombinant urate oxidase) for the Prevention and Treatment of Hyperuricemia During Induction Chemotherapy of Aggressive Non-Hodgkin's Lymphoma: Results of the GRAAL1 Study; J. Clin. Oncol. 2003, 21(23):4402-4406.
Goldman SC et al., A Randomized Comparison Between Rasburicase and Allopurinol in Children with Lymphoma or Leukemia at High Risk for Tumor Lysis, Blood 2001, 97 (10): 2998-3303.
Kissel P. et al., Modificaiton of Uricaemia and the Excretion of Uric Acid Nitrogen by an Enzyme of Fungal Origin, Nature 1968, 217: 72-74.
London M. et al., Uricolytic Activity of Purified Uricase in Two Human Beings, Science 1957, 125:937-938.
Montagnac R. et al. Nephrologie 1990, 11 (4):259.
Moolenburgh JD et al., Rasburicase Treatment in Severe Tophaceous Gout: a Novel Therapeutic Option, Clin. Rheumatol 2005: 1-4.
Richette P. et al., Successful Treatment with Rasburicase of a Tophaceous Gout in a Patient Allergic to Allopurinol, Nature Clinical Practice Rheumatology 2006, 2(6):338-342.
Harris JM et al., Effect of Pegylation on Pharmaceuticals, Nat. Rev. Drug Discov. 2003, 2(3):214-221.
Veronese FM et al., Introduction and Overview of Peptide and Protein Pegylation, Advanced Drug Delivery Reviews 2002, 54(4):453-456.
Kelly SJ et al., Diabetes Insipidus in Uricase-Deficient Mice: A Model for Evaluating Therapy with Poly(Ethylene Glycol)-Modified Uricase, Journal of American Society of Nephrology 2001, 12:1001-1009.
Ganson J. et al., Control of Hyperuricemia in Subjects with Refractory Gout, and Induction of antibody Against Poly(ethylene glycol) (PEG), in a Phase I Trial of Subcutaneous Pegylated Urate Oxidase, Arthritis Res Ther 2005, 8(1):R12.
Motojima, K. et al., Cloning and Sequence Analysis of cDNA for Rat Liver Uricase, J. Biol. Chem. 263:16677-16681, American Society for Biochemistry and Molecular Biology (1988).
Sigma Catalog p. 1002, Product Nos. U 3250, 292-8, U3500, U9375, or U3377 (1993).
Kontsek et al., Forty Years of Interferon, 1997, Acta Virologica, vol. 41, pp. 349-352.
European Examination Report for related European Application No. 01 923 265.1 mailed Dec. 13, 2007, European Patent Office, Munich, DE.
Office Action mailed on Sep. 11, 2003; in related U.S. Appl. No. 09/839,946, Williams et al., filed Apr. 19, 2001.
Office Action mailed on Mar. 5, 2004; in related U.S. Appl. No. 09/839,946, Williams et al., filed Apr. 19, 2001.
Office Action mailed on Aug. 2, 2004; in related U.S. Appl. No. 09/839,946, Williams at al., filed Apr. 19, 2001.
Office Action mailed on Jan. 26, 2005; in related U.S. Appl. No. 09/839,946, Williams et al., filed Apr. 19, 2001.
Office Action mailed on Jul. 20, 2005; in related U.S. Appl. No. 09/839,946, Williams et al., filed Apr. 19, 2001.
Advisory Action mailed on Dec. 5, 2005; in related U.S. Appl. No. 09/839,946, Williams et al., filed Apr. 19, 2001.
Examiner's Answer to Appeal Brief mailed on Jul. 11, 2006; in related U.S. Appl. No. 09/839,946, Williams et al., filed Apr. 19, 2001.
BPAI Decision decided on Jul. 18, 2007; in related U.S. Appl. No. 09/839,946, Williams et al., filed Apr. 19, 2001.
A list of GenBank Accession Numbers corresponding to Uricase Family Member Sequences submitted by Applicants to the Examiner in corresponding South Korean Appl. No. 2001-7001569 on Aug. 24, 2004.
"Chromatography," Practical Application, ed E. Heftman, part 1, Moscow, "Mir," 1986, pp. 104, 108-109.
Becker MA, et al. N. Engl. J. Med. 2005, 353(23): 2450-2461.
Emmerson BT, N. Engl. J. Med. 1996, 334:445-451.
Forrest A., Hawtoff J., Egorin MJ; Evaluation of a New Program for Population PK/PD Analysis Applied to Simulated Phase I Data. Clinical Pharmacology and Therapeuticas 49 (2): 153, 1991.
Mourad G., et al., Presse Med. 1984, 13 (42):2585.
Yamanaka H, et al. Adv. Exp. Med. Biol. 1998, 431:13-18.
Hascall and Heinegard, 1974, J. Biol. Chem. 249:4232-4241, 4242-4249, and 4250-4256.
Heinegard and Hascall, 1974, Arch. Biochem. Biophys. 165:427-441.
Lee et al., 1992, J. Cell Biol. 116: 545-557.
Varelas et al., 1995, Arch. Biochem. Biophys. 321:21-30.
LB Jaques, 1943, Biochem. J. 37:189-195.
AS Jones, 1953, Biochim. Biophys. Acta 10:607-612.
JE Scott, 1955, Chem. And Ind. 168-169.
Smith et al., 1984, J. Biol. Chem. 259:11046-11051.
Cooper JF, 1990, J. Parenter Sci. Technol. 44:13-5.
Kozma et al., 2000, Mol. Cell. Biochem. 203:103-112.
Scott, 1960, Methods Biochem. Anal. 8:145-197.
Laurent et al., 1960, Biochim. Biophys. Acta 42:476-485.
Scott, 1961, Biochem. J. 81:418-424.
Pearce and Mathieson, 1967, Can. J. Biochemistry 45:1565-1576.
Lee, 1973, Fukushima J. Med. Sci. 19:33-39.
Saito, 1955, Kolloid-Z 143:66.
Blumberg and Ogston, 1958, Biochem. J. 68:183-188.
Matsumura et al., 1963, Biochim, Biophys. Acta 69:574-576.
Serafini-Fracassini et al., 1967, Biochem. J. 105:569-575.
Potaux, L. et al., 1975, Nouv. Presse Med. 4:1109-1112.
Adv. Exp. Med. Biol., 1994, 366:377-387.
Ben-Bassat and Bauer,1987, Nature 326:315.
Otta and Bertini, 1975, Acta Physiol. Latinoam, 25:451-457.
Truscoe, 1967, Enzymologia 33:1 19-32.
Antonopoulos et al., 1961, Biochim. Biophys. Acta 54:213-226.
Embery, 1976, J. Biol. Buccale 4:229-236.
Rinella et al., 1998, J. Colloid Interface Sci. 197:48-56.
Maccari and Volpi, 2002, Electrophoresis 23:3270-3277.
Scott, 1955, Biochim. Biophys. Acta 18:428-429.
Leaustic M. et al., 1983, Rev. Rhum. Mal. Osteoartic 50:553-554.
Montalbini, P. et al., Isolation and characterization of uricase from bean leaves and its comparison with uredospore enzymes, Plant Sci. 147:139-147, Elsevier Science Ireland Ltd. (May 1999).
Kelly, S. J., M. Delnomdedieu, et al. (2001) as "Diabetes insipidus in uricase-deficient mice: A model for evaluating therapy with poly(ethylene glycol)-modified uricase." in J Am Soc Nephrol 12: 1001-1009.

Lee et al., (Sep. 2005) as "Arthritis & Rheumatism" in the Official Journal of the American College of Rheumatology, Abstract Supplement, vol. 52, No. 9, p. S105.

Office Action dated Jan. 26, 2010, U.S. Appl. No. 11/918,296, filed Dec. 11, 2008, Inventor Jacob Hartman.

Office Action dated Oct. 30, 2009, U.S. Appl. No. 11/899,688, filed Sep. 7, 2007, Inventor Jacob Hartman.

Sundy, J.S. et al., A Phase I Study of Pegylated-Uricase (Puricase®) in Subjects with Gout, Arthritis Rheum. 2004 vol. 50, supplement 9, S337-338.

Sundy, J.S. et al., A Phase I Study of Pegylated-Uricase (Puricase®) in Subjects with Gout, presented at American College of Rheumatology Annual Scientific Meeting on Oct. 16-21, 2004 at San Antonio, TX, Poster 807.

Ganson, N.J. et al., Antibodies to Polyethylene Glycol (PEG) during Phase I Investigation of PEG-Urate Oxidase (PEG-uricase; Puricase®) for Refractory Gout, Arthritis Rheum. 2004 vol. 50, supplement 9, S338.

Ganson, N.J. et al., Antibodies to Polyethylene Glycol (PEG) during Phase I Investigation of PEG-Urate Oxidase (PEG-uricase; Puricase®) for Refractory Gout, presented at American College of Rheumatology Annual Scientific Meeting on Oct. 16-21, 2004 at San Antonio, TX, Poster 808.

Baraf H. et al., Resolution of Tophi With Intravenous Peg-uricase in Refractory Gout, Arthritis & Rheumatism, Sep. 2005, Supplement, vol. 52, No. 9, p. S105.

Baraf H. et al., Resolution of Tophi With Intravenous Peg-uricase in Refractory Gout, presented at American College of Rheumatology 2005 Annual Scientific Meeting on Nov. 13-17, 2005 at San Diego, CA, Poster 194.

Sundy, J.S. et al., A Phase 2 Study of Multiple Doses of Intravenous Polyethylene Glycol (PEG)-uricase in Patients with Hyperuricemia and Refractory Gout, presented at American College of Rheumatology 2005 Annual Scientific Meeting on Nov. 13-17, 2005 at San Diego, CA, #1836.

Baraf H. et al., Resolution of Tophi With Intravenous Peg-uricase in Treatment-Failure Gout, Ann Rheum Dis. 2006: 65 (Suppl. II), 256, Poster 465.

Baraf H. et al., Resolution of Tophi With Intravenous Peg-uricase in Treatment-Failure Gout, presented at the EULAR—Annual European Congress of Rheumatology, on Jun. 21-24, 2006 at Amsterdam, Netherlands, Poster 465.

Sundy, J.S. et al., A Phase 2 Study of Multiple Doses of Intravenous Polyethylene Glycol (PEG)-uricase in Patients with Hyperuricemia and Refractory Gout, Ann Rheum Dis. 2006: 65 (Suppl. II), 271, Poster 516.

Sundy, J.S. et al., A Phase 2 Study of Multiple Doses of Intravenous Polyethylene Glycol (PEG)-uricase in Patients with Hyperuricemia and Refractory Gout, presented at the EULAR—Annual European Congress of Rheumatology, on Jun. 21-24, 2006 at Amsterdam, Netherlands, Poster 516.

Sundy, J.S. et al., Quality of Life in Patients With Treatment-Failure Gout, Ann Rheum Dis. 2006: 65 (Suppl. II), 271, Poster 517.

Sundy, J.S. et al., Quality of Life in Patients With Treatment-Failure Gout, presented at the EULAR—Annual European Congress of Rheumatology, on Jun. 21-24, 2006 at Amsterdam, Netherlands, Poster 517.

Sundy, J.S. et al., A Multicenter Longitudinal Study of Disease Characteristics in Patients With Treatment-Failure Gout, Ann Rheum Dis. 2006: 65 (Suppl. II), 272, Poster 518.

Sundy, J.S. et al., A Multicenter Longitudinal Study of Disease Characteristics in Patients With Treatment-Failure Gout, presented at the EULAR—Annual European Congress of Rheumatology, on Jun. 21-24, 2006 at Amsterdam, Netherlands, Poster 518.

Seng Yue, C. et al., Population Pharmacokinetic and Pharmacodynamic Analysis of PEG-uricase in Subjects With Hyperuricemia and Refractory Gout, presented at the American College of Clinical Pharmacy 2006 Annual Meeting on Oct. 26-29, 2006 at St. Louis, Missouri, Poster.

* cited by examiner

METHODS FOR LOWERING ELEVATED URIC ACID LEVELS USING INTRAVENOUS INJECTIONS OF PEG-URICASE

The present application is a continuation-in-part of PCT/US2006/013660 and PCT/US2006/013502, both of which were filed Apr. 11, 2006 and which claim priority and benefit of U.S. Provisional Applications Ser. Nos. 60/670,573, filed Apr. 11, 2005 and 60/670,541, filed Apr. 11, 2005 respectively. The disclosure of PCT/US2006/013660 and PCT/US2006/013502 as well as U.S. Provisional Applications Ser. Nos. 60/670,573 and 60/670,541 are hereby incorporated by reference herein in their entireties.

FIELD OF THE INVENTION

The invention relates to methods for lowering elevated uric acid levels using intravenous injections of PEG-Uricase.

BACKGROUND OF THE INVENTION

Throughout this application, various publications are referenced within the text. The disclosures of these publications in their entireties are hereby incorporated by reference into this application in order to more fully describe the state of the art as known to those skilled therein as of the date of the invention described and claimed herein.

When less uric acid is excreted than is produced, plasma urate concentration (pUAc) rises and may exceed the limit of solubility (~7 mg/dL or 0.42 mM), causing the deposition of monosodium urate (MSU) in tissues. In susceptible individuals intra-articular MSU crystals trigger inflammatory attacks of gout (Becker M A: Hyperuricemia and gout. In: *The Metabolic and Molecular Bases of Inherited Disease.* Edited by Scriver C R, Beaudet A L, Sly W S, Valle D, 8th edn. New York: McGraw-Hill; 2001: 2513-2535; Terkeltaub R A: Clinical practice. Gout. *N Engl J Med* 2003, 349(17):1647-1655; and Wortmann R L et al.: Gout and Hyperuricemia. In: *Kelley's Textbook of Rheumatology.* Edited by Ruddy S, Harris E D, Jr., Sledge C B, 6th edn. St. Louis: W. B. Saunders; 2001: 1339-1371).

Blocking urate production by inhibiting xanthine oxidase, or promoting renal urate excretion, can prevent further MSU crystal accumulation in tissues if plasma urate concentration is maintained below 6 mg/dL (Li-Yu J et al. *J Rheumatol* 2001, 28(3):577-580; Perez-Ruiz F, et al. *Arthritis Rheum* 2002, 47(4):356-360; and Shoji A, et al. *Arthritis Rheum* 2004, 51(3):321-325). If hyperuricemia is poorly controlled, gout may become chronic, leading to arthropathy, nephropathy, and various complications of tophi. Conventional therapy may be less effective at this stage since expanded tissue stores may only slowly be depleted by blocking new urate production, particularly if urate excretion is impaired by renal insufficiency, or by concomitant therapy with diuretics or cyclosporine.

Most mammals can convert uric acid to the more soluble compound allantoin. This metabolic route of elimination is inoperative in humans owing to mutation of the urate oxidase (uricase) gene during evolution. Parenteral uricase derived from *Aspergillus flavus* (Rasburicase, Sanofi Synthelabo) is effective in preventing acute uric acid nephropathy in patients with malignancies (Coiffier B. et al. *J Clin Oncol* 2003, 21(23):4402-4406; and Goldman S C, et al. *Blood* 2001, 97(10):2998-3003). This and other uricase preparations have been used with apparent benefit to treat small numbers of patients with refractory gout (Kissel P. et al. *Nature* 1968, 217:72-74; London M, et al. *Science* 1957, 125:937-938; Montagnac R. et al. *Nephrologie* 1990, 11(4):259; Moolenburgh J D, et al. *Clin Rheumatol* 2005:1-4; Mourad G. et al. *Presse Med* 1984, 13(42):2585; and Richette P, et al. *Nature Clinical Practice Rheumatology* 2006, 2(6):338-342). However, no clinical trials for this indication have been reported, and a relatively short circulating life and potential immunogenicity have limited their wider application for treating gout.

Attaching the inert polymer polyethylene glycol (PEG) to proteins can extend their circulating life and diminish immune recognition (Abuchowski A, et al. *J Biol Chem* 1977, 252(11):3582-3586; Harris J M, et al. *Nat Rev Drug Discov* 2003, 2(3):214-221; Veronese F M, et al. *Adv Drug Deliv Rev* 2002, 54(4):453-456. The development of a PEGylated recombinant mammalian uricase for treating gout is being pursued (Kelly S J, et al. *J Am Soc Nephrol* 2001, 12:1001-1009). In an initial Phase I clinical trial, 13 subjects with severe gout and mean pUAc >11 mg/dL received single subcutaneous (SC) injections of 4 to 24 mg of PEG-uricase (Ganson N J, et al. *Arthritis Res Ther* 2005, 8(1):R12). Within 7 days, pUAc fell by a mean of ~8 mg/dL, and normalized in 11 subjects. At doses of 8-24 mg, mean pUAc remained <6 mg/dL at 21 days post-injection. Although very effective, SC-injected PEG-uricase caused transient local pain and was slowly absorbed. It was also rapidly cleared in 5 subjects who developed antibodies that, unexpectedly, reacted with PEG rather than with the uricase protein. Three of the latter subjects had allergic reactions that began at the injection site at 8-9 days post-injection (Ganson N J, et al. *Arthritis Res Ther* 2005, 8(1):R12).

SUMMARY OF THE INVENTION

The present invention provides a method for lowering elevated uric acid levels in a patient comprising administering to said patient an intravenous injection of PEG-uricase having a dosage from about 4 to about 12 mg.

Other objects and advantages of the present invention will become apparent from the following description and appended claims.

BRIEF DESCRIPTION OF THE DRAWINGS

FIG. 1A shoaws the plasma uricase activity (pUox, circles) and plasma uric acid concentration (pUAc, triangles) following a single IV infusion of 8 mg of PEG-uricase. Values plotted are the means ± sd for 4 subjects. FIG. 1B shows the relationship of PEG-uricase dosage to the maximum level of plasma uricase activity (pUox, Cmax, circles) and minimum plasma uric acid concentration (pUAc, Cmin, triangles) achieved after single IV infusions. Values plotted are the means ± sd for 4 subjects. FIG. 1C shows the relationship between PEG-uricase dosage and Area Under Concentration curve (AUC) for plasma uricase activity (pUox, circles) and plasma uric acid concentration (pUAc, triangles) after single intravenous (IV) infusions (solid lines), or single subcutaneous (SC) injections (longer dashed lines). The values for SC administration are calculated from data obtained in a previous study (Ganson N J, et al. *Arthritis Res Ther* 2005, 8(1):R12). For each parameter, AUC was calculated from data obtained for 21 d post infusion or injection. AUC units for pUox=mU/mL·hr; AUC units for pUAc=mg/dL·hr. Values plotted are the means for 4 subjects treated at each dose level. The horizontal fine dashed line indicates the theoretical AUC value that would be obtained if pUAc was constant at 6 mg/dL for 21 d.

DETAILED DESCRIPTION OF THE INVENTION

Figure 1A:
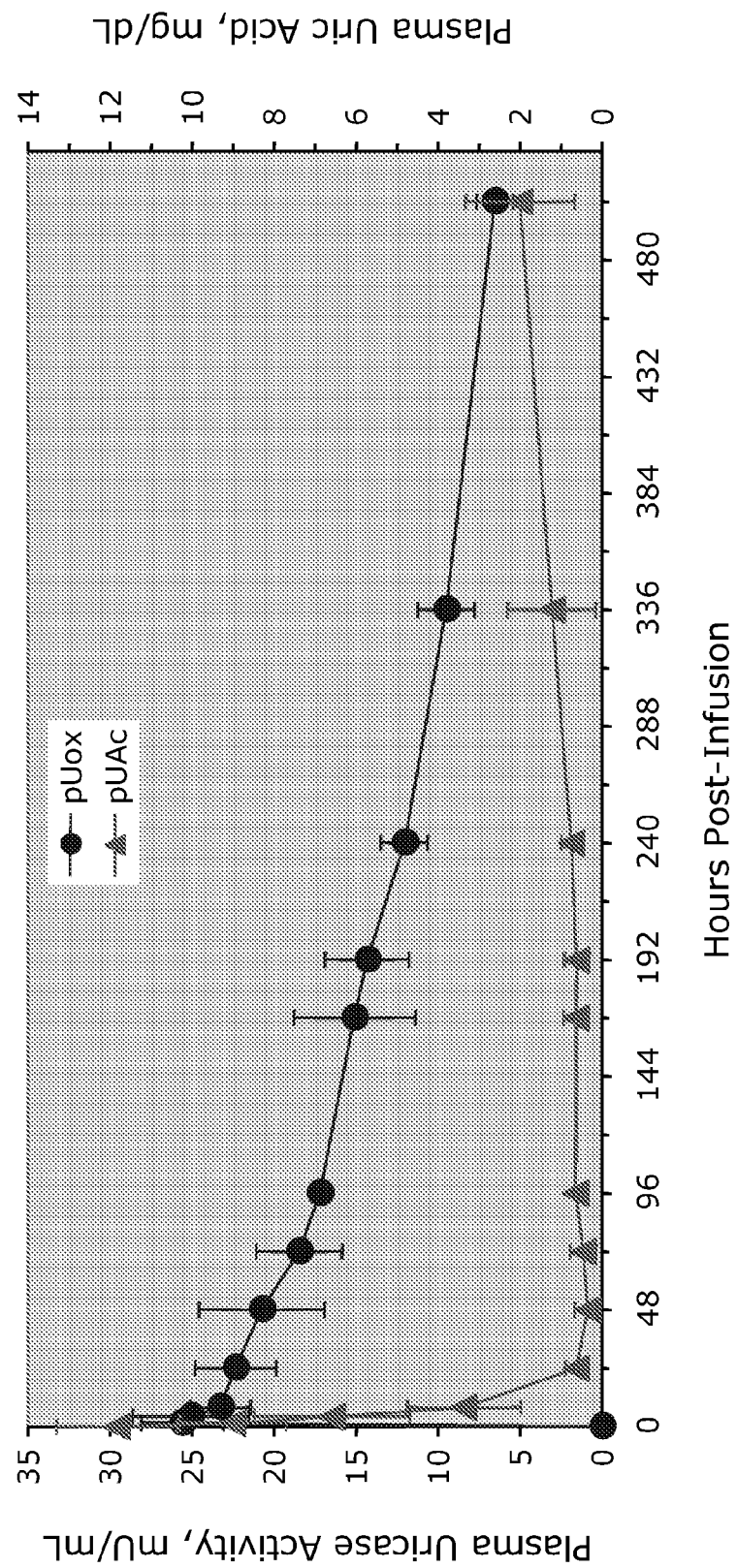
FIGS. 1A-1C show pharmacokinetics and pharmacodynamics of intravenous PEG-uricase.

It has been surprisingly discovered that IV PEG-uricase is superior to subcutaneous (SC) enzyme injections in achieving a more rapid, significant, and prolonged lowering of plasma urate concentration (pUAc), and it greatly reduces urinary uric acid excretion. Furthermore, while single infusions of PEG-uricase induced anti-PEG antibodies in some subjects, no allergic reactions were encountered.

The dosage of IV injections of PEG-Uricase is from about 0.5 to about 12 mg, preferably from about 4 to about 12 mg. PEG-Uricase may also be administered by IV injection in dosages between 4 and 8 mg, or between 8 and 12 mg.

The uricase used in PEG-Uricase may comprise a mammalian uricase amino acid sequence truncated at the amino terminus or the carboxy terminus or both the amino and carboxy termini by about 1-13 amino acids and may further comprise an amino acid substitution at about position 46. The truncated uricase may further comprise an amino terminal amino acid, wherein the amino terminal amino acid is alanine, glycine, proline, serine, or threonine as described in co-pending PCT/US2006/013660 and U.S. provisional application Ser. No. 60/670,573, which are hereby incorporated herein by reference in their entireties.

A Phase I study of single IV infusions of PEG-uricase in 24 hyperuricemic subjects with severe gout was completed as indicated in the Examples below. A Phase I trial of subcutaneously injected enzyme in 13 such patients was previously carried out (Ganson N J, et al. *Arthritis Res Ther* 2005, 8(1): R12). Both trials examined PEG-uricase at doses of 4, 8 and 12 mg in groups of 4 subjects, and monitored study parameters for 21 days after dosing (lower doses of 0.5, 1 and 2 mg were also tested in the present trial). The results of these two trials have established suitable conditions of dose and the frequency and route of administration for use in later stages in the clinical evaluation of PEG-uricase.

PEG-uricase is intended for patients with poorly controlled hyperuricemia who have failed other forms of therapy. Subjects in the present (and previous) trial had recent or continuous clinical manifestations of gout; 75% had tophi. In none had a therapeutic serum urate concentration (<6.0 mg/dL) been adequately maintained with available urate lowering medications (whether this was due to noncompliance, lack of efficacy at prescribed dosages, or to drug intolerance was not considered in selecting subjects for this Phase I trial). The mean pUAc prior to infusion of PEG-uricase was 10.9±0.5 mg/dL. In most subjects uricase activity was detectable in plasma for the full 21-day post-infusion period of observation.

The pharmacodynamic results of most interest were obtained with doses of 4, 8, and 12 mg, which were most effective in lowering urate levels in plasma and urine. The onset of action was rapid: mean pUAc fell to <2 mg/dL within 24 h post-infusion, and the maximum decline in pUAc from baseline averaged 10.3 mg/dL at 24-72 h. Of importance, the AUC for the entire 21-d period post-infusion was equivalent to maintaining a constant pUAc of 4.7, 1.2, and 2.7 mg/dL at PEG-uricase doses of 4, 8, and 12 mg, respectively. This prolonged lowering of pUAc to below the therapeutic target of 6 mg/dL is more impressive in view of the level of disease and inadequate response of these subjects to conventional therapy. Comparison of AUC data for both pUox and pUAc at doses of 4-12 mg obtained in the present and previous trial (FIG. 1C) clearly indicates the superior bioavailability and efficacy of IV versus SC PEG-uricase.

Single infusions of PEG-uricase in the 4 to 12 mg range also markedly lowered the UAc:Cr ratio in urine in parallel with the effect on pUAc. Measuring UAc:Cr in spot urine samples might provide an alternative way to monitor the response to PEG-uricase therapy, with the advantage of not requiring measures to inhibit PEG-uricase, as is necessary to accurately assess the effect on serum/plasma urate concentration. The ability to greatly reduce or eliminate uric acid excretion could be of particular benefit in patients with uric acid nephrolithiasis, which may complicate chronic gout.

The results with single infusions of PEG-uricase indicated that doses of about 4 to 12 mg at intervals of 2 to 4 weeks would maintain a therapeutic response.

Infused PEG-uricase was generally well tolerated, and all adverse events were classified as mild or moderate; their frequency was unrelated to dose. The only adverse events considered possibly related to PEG-uricase were gout flares and arthralgia in 14 subjects. The present study population reported frequent gout flares prior to the trial, and reducing serum urate concentration with other drugs has also been associated with an increased incidence of gout flares (Becker M A, et al. *N Engl J Med* 2005, 353(23):2450-2461; Emmerson B T, *N Engl J Med* 1996, 334:445-451; and Yamanaka H, et al. *Adv Exp Med Biol* 1998, 431:13-18.

IgG antibodies to PEG-uricase, in most cases of the IgG2 subclass and specific for PEG, developed in 9 out of 24 Phase I subjects. There was a trend toward more rapid terminal clearance of PEG-uricase in the antibody-positive subjects. However, in contrast to the cutaneous reactions in 3 of 5 antibody-positive subjects treated with SC PEG-uricase (Ganson N J, et al. *Arthritis Res Ther* 2005, 8(1):R12.), no allergic reactions occurred in the present trial. Also, whereas several subjects developed local pain and swelling within a few hours of receiving SC injections of PEG-uricase, there were no infusion reactions in the present study.

Hydrogen peroxide ($H_2O_2$), a byproduct of urate oxidation, was postulated to cause inflammation at the SC injection site, which, along with the slow absorption of SC PEG-uricase, may have contributed to antibody development and late allergic reactions (Ganson N J, et al. *Arthritis Res Ther* 2005, 8(1):R12). In considering the absence of infusion and delayed allergic reactions in the present study, it is significant that infused PEG-uricase is largely confined to the intravascular space where very high levels of catalase in red cells can efficiently eliminate $H_2O_2$ produced in plasma. Also, since $H_2O_2$ is only generated by PEG-uricase as urate is oxidized, the rate of intravascular $H_2O_2$ production would decrease markedly within 24 h of the infusion of PEG-uricase if pUAc is maintained close to or below 1 mg/dL.

The results herein indicate that IV doses of about 0.5 to 12 mg of PEG-uricase administered every 2-4 weeks will maintain plasma urate well below 6 mg/dL, and will be effective in rapidly reducing tophus size. PEG-uricase may also be used in patients with chronic gout and hyperuricemia that is poorly controlled with existing therapies.

EXAMPLE 1

Material, Methods and Design of Clinical Study

Investigational Drug

PEG-uricase consists of a recombinant mammalian uricase (primarily porcine, with C-terminal sequence from baboon uricase), conjugated with multiple strands of monomethoxyPEG of average molecular weight 10 kDa (10 K mPEG) per subunit of tetrameric enzyme (Kelly S J, et al. *J Am Soc Nephrol* 2001, 12:1001-1009; and Ganson N J, et al. *Arthritis Res Ther* 2005, 8(1):R12). It was manufactured by Savient Pharmaceuticals, Inc. (East Brunswick, N.J.) and supplied in vials containing 12.9 mg of PEG-uricase (233 Units, assayed as described below) in 1 mL of a phosphate buffer.

Phase I Study Design

An open-label study was conducted in 24 adults with symptomatic gout, who were assigned sequentially to 6 cohorts of 4 subjects each, to receive single IV infusions lasting 60 minutes and containing 0.5, 1, 2, 4, 8, or 12 mg of PEG-uricase in 50 mL of saline. The protocol and consent form were approved by the Duke University Institutional Review Board. Uric acid lowering medications were withheld for 7 days prior to, and for 21 days after dosing. The primary outcomes were the pharmacokinetics and safety of PEG-uricase. Secondary outcomes were the effects of PEG-uricase on pUAc, and on the ratio of uric acid to creatinine in urine (UAc:Cr). Adverse events and changes in clinical laboratory tests were used to assess safety for 35 days after dosing. Pharmacokinetic and pharmacodynamic parameters were assessed for 21 days after dosing. The IgG antibody response to PEG-uricase was assessed prior to, and on days 7, 14, and 35 post-infusion.

Subjects

Inclusion requirements were: age $\geq 18$ years; symptomatic gout (tophi, chronic synovitis due to gout, or gout flare within the last 6 months); and a pUAc $\geq 7$ mg/dL after discontinuing uric acid lowering therapy for at least 7 days. Subjects were excluded for any of the following: unstable coronary artery disease; uncontrolled hypertension; renal insufficiency requiring dialysis; baseline serum aminotransferase levels >1.5 times the upper limit of normal in the absence of known cause; organ transplantation requiring immunosuppressive therapy; requirement for corticosteroid at a dose of >10 mg of prednisone (or equivalent) within one week of dosing; continued use of uric acid lowering medications; acute gout flare at baseline; glucose-6-phosphate dehydrogenase deficiency; or previous administration of urate oxidase.

Pharmacokinetic and Pharmacodynamic Measurements

PEG-uricase was monitored as uricase catalytic activity in plasma (pUox) as described (Ganson N J, et al. *Arthritis Res Ther* 2005, 8(1):R12). Results are expressed as mU per mL plasma, where 1 U=1 μmol of urate oxidized per min. Plasma urate concentration (pUAc) was measured after acidification to inactivate PEG-uricase (Ganson N J, et al. *Arthritis Res Ther* 2005, 8(1):R12).

Immune Response to PEG-Uricase

ELISAs for IgG antibodies to PEG-uricase and to 10 K mPEG-glycine (10 K mPEG conjugated with glycine instead of uricase protein) were performed in the Hershfield laboratory as described (Ganson N J, et al. *Arthritis Res Ther* 2005, 8(1):R12]. Screening was performed on dilutions (1:20 and 1:60) of pre-dose (day 0), day 14, day 21, and day 35 plasma samples. Plasma from an antibody-positive (i.e. to both PEG-uricase and 10 K mPEG-glycine) subject identified in the previous Phase I trial of SC PEG-uricase (Ganson N J, et al. *Arthritis Res Ther* 2005, 8(1):R12) was used as a positive reference. A "positive" ELISA was defined as an absorbance at 405 nm (A405) >3 sd above the mean for a panel of plasma samples from naive subjects.

The IgG subclass of antibodies binding specifically to PEG-uricase immobilized on an ELISA plate was determined with mouse anti human IgG1, IgG2, IgG3, and IgG4-specific antibodies (Sigma, St. Louis, Mo.).

Other Laboratory Studies

A routine chemistry panel, complete blood count (CBC), glucose-6-phosphate dehydrogenase, and haptoglobin were obtained at screening visit. Pregnancy was excluded by serum beta-HCG in women of child-bearing potential. C-reactive protein, erythrocyte sedimentation rate, and complement proteins C3 and C4, C1q binding assay, and CH50 were measured prior to dosing and on days 3, 10, 14 and 21 after dosing, along with a chemistry panel, CBC, and haptoglobin.

Evaluation of Safety

Subjects were monitored for 35 d after receiving PEG-uricase. Adverse events, including gout flares, detected by study personnel, or elicited from or volunteered by study subjects were recorded. Gout flares were treated according to the judgment of the study physician.

EXAMPLE 2

Clinical Study Using Infusion of PEG-Uricase

A clinical study was carried out as indicated in Example 1 above. The results are indicated below Subject Characteristics The demographic and gout disease characteristics of study subjects are shown in Table 1 below. Common co-morbidities associated with gout, including obesity, hypertension, coronary artery disease, and renal stones, were distributed relatively evenly among the 6 dosing cohorts, although 3 of 4 subjects in the 4 mg cohort had type II diabetes mellitus. Mean age ranged from 41.8 y in the 2 mg, to 64.5 y in the 12 mg dose cohort. Mean body mass index ranged from 28.3 in the 2 mg, to 36.5 in the 8 mg dose cohorts.

TABLE 1

Characteristics of Phase I Trial Subjects

| | |
|---|---|
| Gender | Female 4, male 20 |
| Age (y) | 56.7 ± 12.9 (28-73) |
| Number of subjects with: | acute gout attacks, 22 (92%); chronic synovitis, 15 (62.5%); tophi, 18 (75%); nephrolithiasis, 5 (21%) |
| Body Mass Index | 32.2 ± 6.6 (23.4-49.2) |
| Serum Uric Acid* | On allopurinol (7 subjects): 6.6 ± 1.2 mg/dL (4.8-7.8) Not on allopurinol (17 subjects): 9.4 ± 0.9 mg/dL (7.2-12.3) |
| Serum Creatinine* | 1.2 ± 0.4 mg/dL (0.8-2.2) |
| Most frequent co-morbidities | hypertension, 16; diabetes, 6; osteoarthritis, 6; cardiac dysrhythmias, 6; coronary artery disease, 3. |

*Values measured prior to the drug washout period

A history of acute gout attacks was reported by 92% of subjects; flares were monoarticular in 41%, oligoarticular in 27%, and polyarticular in 32%. Chronic synovitis was present in 62.5% of subjects and 75% had tophi. At screening, the mean ± sd serum urate concentration was 9.4±0.9 mg/dL in the 17 subjects who were not receiving antihyperuricemic medication, and 6.6±1.2 mg/dL in the 7 subjects who were receiving allopurinol. After the washout period pUAc in the latter subjects rose to 8.6±0.8 mg/dL.

Pharmacokinetics and Pharmacodynamics with Single Infusions of PEG-Uricase

Prior to infusion of PEG-uricase, the mean ± sd pUAc for all 6 dose cohorts was 10.9±0.5 mg/dL (range 10.7-11.8 mg/dL); pUox was undetectable in all subjects. FIG. 1A plots these parameters following infusion of PEG-uricase for the 8 mg dose cohort, which had the highest baseline pUAc. Maximum post-infusion pUox was 26±2.8 mU/mL, and the level after 21 d was 6.5±1.1 mU/mL; the plasma half-life for pUox was 300±21 h (12.5±0.9 d). Within 24 h of dosing, mean pUAc had decreased by 11.2 mg/dL, and reached a nadir of 0.3 mg/dL at 72 h post-infusion. At 21 d, the mean pUAc was 2 mg/dL, or 9.8 mg/dL below baseline.

Figure 1B:
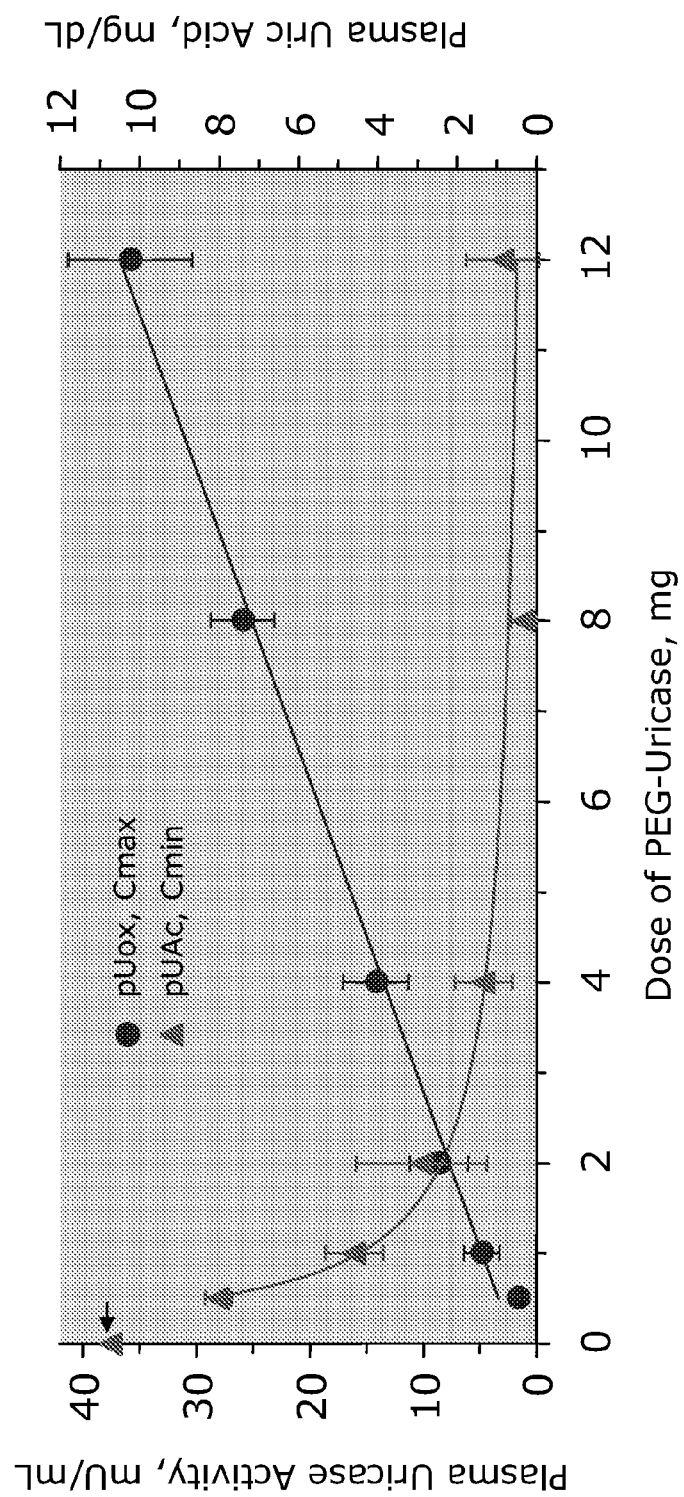

Maximal pUox (Cmax) increased linearly with dose of PEG-uricase (FIG. 1B). The nadir value for pUAc (Cmin) declined steeply at doses of 0.5-2mg and was <1.5 mg/dL at doses of 4-12 mg, with an average reduction of 10.3 mg/dL (range 9.5-11.5 mg/dL) below baseline. Cmin for pUAc occurred at 48-72 h post-infusion for the 1-8 mg dose cohorts, and at 24 h in 3 of 4 subjects in the 12 mg cohort. Mean half-life for pUox for the 6 dose cohorts was 220±77 h (9.2±3.2 d), with a range from 163-332 h (6.4-13.8 d). The volume of distribution for PEG-uricase ranged from about 5,000 to 10,000 mL.

Figure 1C:
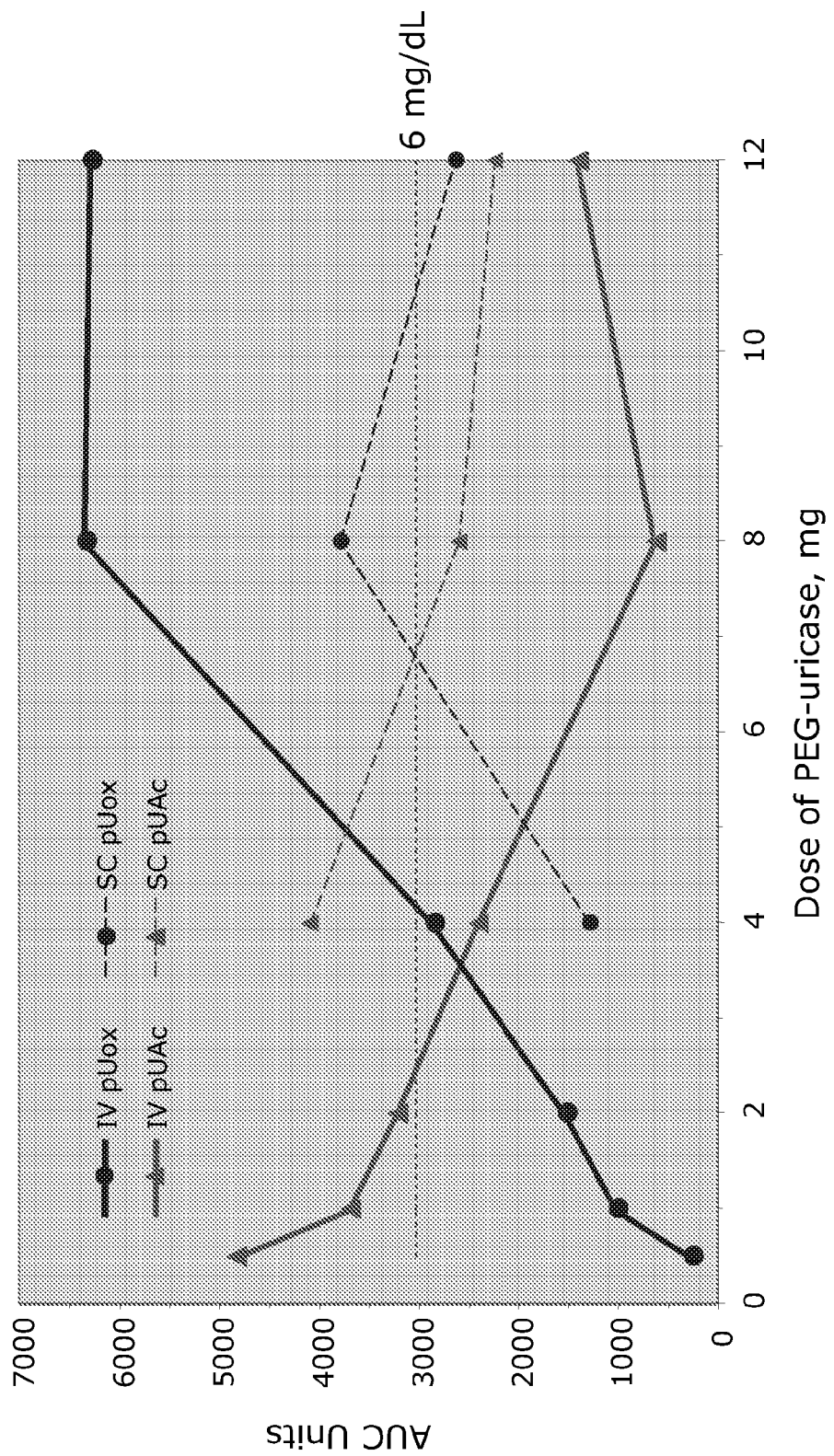

Area-under-concentration curve (AUC) parameters for pUox and pUAc were inversely related to one another, and were each proportional to the dose of PEG-uricase between 0.5 and 8 mg (FIG. 1C). Doses of 4, 8, and 12 mg resulted in AUC values for pUAc equivalent to maintaining constant pUAc levels of 4.7, 1.2, and 2.7 mg/dL, respectively, for 21 d post-infusion. The superior bioavailability and efficacy of IV compared with SC administration is evident.

Effect of PEG-Uricase on Urinary Excretion of Uric Acid

Figure 2:
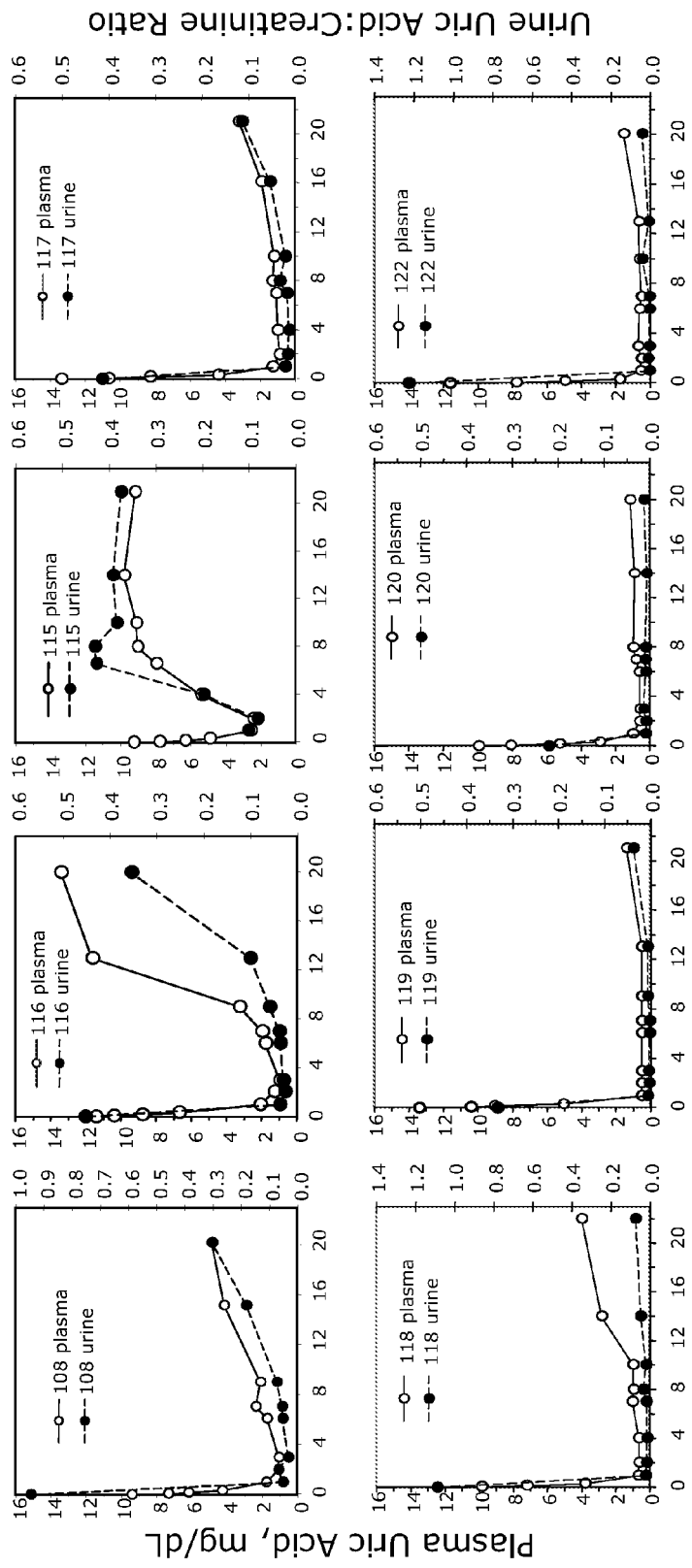
FIG. 2 shows the relationship between plasma uric acid concentration (mg/dL, left axis, open circles), and the ratio of uric acid:creatinine in urine (right axis, solid circles, dashed line). Upper panels show data for individual study subjects who received IV infusions of 4 mg PEG-uricase; lower panels show data for subjects who received 8 mg infusions.

Infusion of PEG-uricase markedly reduced renal uric acid excretion, as indicated by a decline in UAc:Cr in spot urine samples. This is illustrated for the 4 mg and 8 mg dose cohorts in FIG. 2, which also shows coordinate effects on pUAc and urinary UAc:Cr.

Immune Response to IV PEG-Uricase

Figure 3:
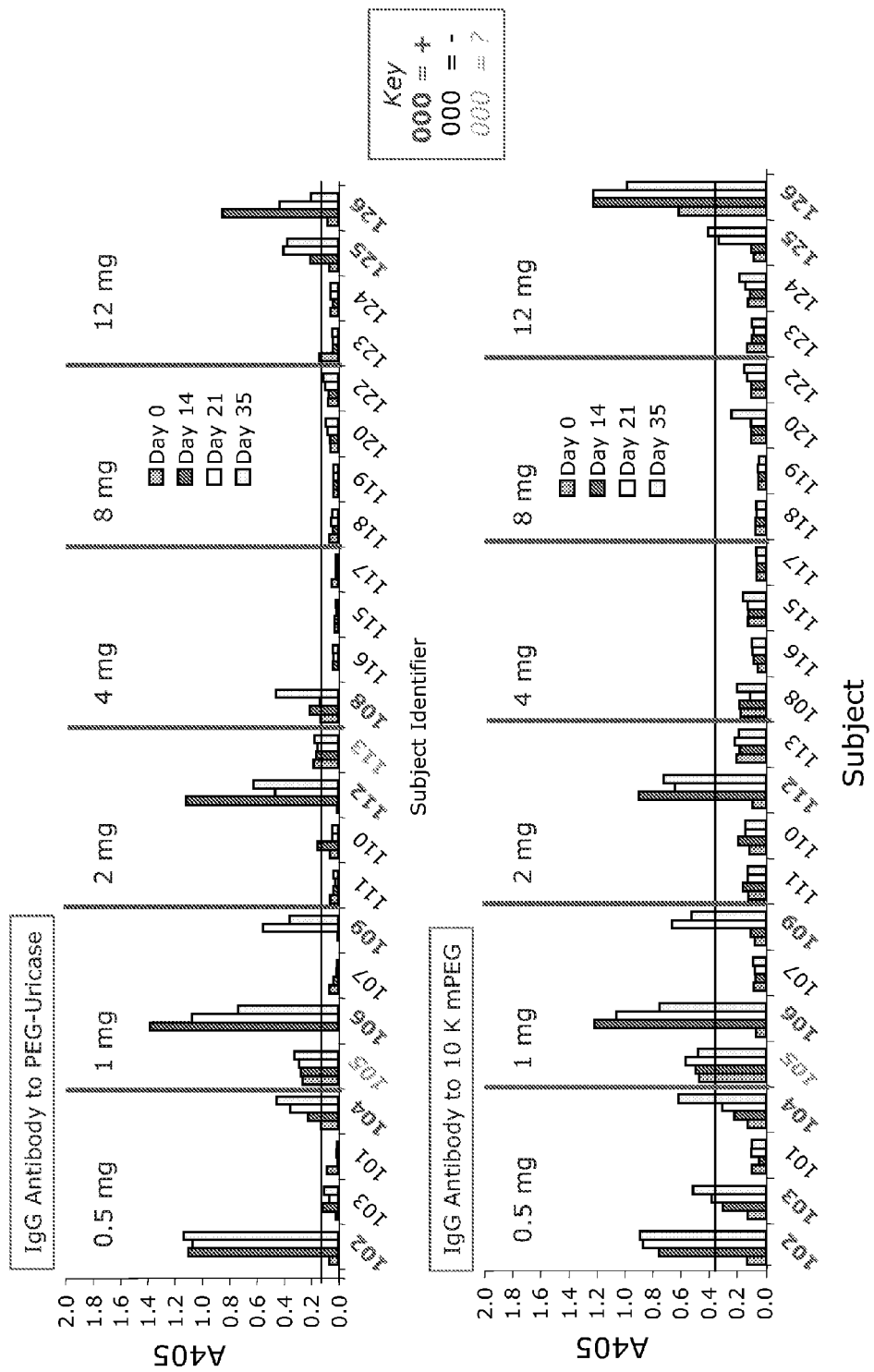
FIG. 3 shows ELISAs for IgG antibodies to PEG-uricase (upper panel) and to 10 K mPEG (lower panel) in 24 Phase I study subjects. Plasma samples tested were obtained prior to (day 0), and on days 14, 21, and 35 following a single intravenous infusion of the indicated dose of PEG-uricase. Horizontal lines above the X-axis represents the mean +3 sd values obtained in each ELISA for a panel of normal individuals, which serve as the cutoff for scoring samples from study subjects as positive or negative in the ELISA. The 'Key' legend indicate whether a subject has "sero-converted" from a negative to a positive ELISA response after infusion of PEG-uricase (black numbers, negative; bold red numbers, positive). In 2 cases where the day 0 sample exceeded the cutoff value (italicized orange numbers), the result was considered indeterminate.

Prior to treatment, 22 of the 24 Phase I subjects had negative ELISAs for IgG antibodies to both PEG-uricase (FIG. 3A) and 10 K mPEG (FIG. 3B). Both ELISAs remained negative in 13 of these subjects when tested again at d 14, 21, and 35 post-infusion. The other 9 subjects developed positive ELISAs, in 7 cases for both antigens, and in 2 cases for one or the other antigen. Studies not presented showed that antibodies that reacted with PEG-uricase and 10 K mPEG were of the IgG2 subclass, or in some cases both IgG2 and IgG3.

Antibody testing was inconclusive in 2 Phase I subjects who had positive ELISAs at baseline, which did not change significantly after infusion of PEG-uricase. Plasma from subject 113 reacted with PEG-uricase, but not with 10 K mPEG, whereas plasma from subject 105 was positive with both antigens. Of interest, in this latter subject pUox was only detected transiently during the first 24 h after infusion, compared with detectable pUox levels for 7 to 21 d in the 3 other subjects in the 1 mg dose cohort (data not shown).

In a previous trial, IgG antibody to PEG-uricase appeared at 7 days after SC administration, about when pUox was maximal owing to slow absorption from the injection site (Ganson N J, et al. *Arthritis Res Ther* 2005, 8(1):R12). In antibody-positive subjects pUox declined rapidly from this peak to undetectable levels by day 10-14 post infusion. In the present study, a trend towards more rapid terminal clearance of infused PEG-uricase was indicated by the finding that pUox could last be detected at 11.0±6.0 d (range 4-21 d) in ELISA-positive, vs. 16.1±5.9 d (range 4-22 d) in ELISA-negative subjects (p=0.06 in a 2-tailed T test).

Evidence of antibody-mediated clearance was also obtained when antibody-positive subject 109 in the 1 mg dose cohort was given a second infusion of 8 mg of PEG-uricase about a year after his exposure in the Phase 1 trial. The ELISA to PEG-uricase had become negative prior to the second infusion, but became strongly positive again by 7 d after dosing. For 48 h after infusion, pUox levels were consistent with this 8 mg dose of PEG-uricase, causing pUAc to decline by 10 mg/dL. However, on d 7 post-infusion, pUox was undetectable (whereas it was measurable for 9 d after the first 1 mg dose), and pUAc had returned to the pre-infusion level. No allergic phenomena were associated with this anamnestic antibody response.

Safety and Tolerability

All 24 Phase I subjects completed the study. There were no serious adverse events or clinically important changes in laboratory results. Twenty-two Phase I subjects experienced 66 adverse events, all of mild to moderate severity (Table 2). Twenty-one of these were considered possibly related to study treatment; all but one were gout flares, the other being arthralgia. The risk of an adverse event was similar in each dosing cohort. None of the subjects experienced infusion reactions.

TABLE 2

Adverse Events

| | |
|---|---|
| Total subjects | 24 |
| Number of Subjects with Events | 22 (92%) |
| Gout | 14 (58.3%) |
| Blood pressure increased | 2 (8.3%) |
| Arthralgia | 4 (16.7%) |
| Back pain | 2 (8.3%) |
| Diarrhoea nos | 2 (8.3%) |
| Dyspepsia | 2 (8.3%) |
| Dizziness | 3 (12.5%) |
| Upper respiratory tract infection nos | 2 (8.3%) |
| Insomnia | 2 (8.3%) |
| Other (occurring in one subject): hyperglycemia, hypokalemia, anemia, headache, pruritus, sweating, aesthenia, peripheral edema, fever, herpes simplex, hypotension | 10 |

The most common adverse event was acute gout flare (20 flares in 14 study subjects). The number of subjects experiencing a gout flare was 0 in the 0.5 mg cohort; 2 in 1 mg and 12 mg cohorts; 3 in the 2 mg and 4 mg cohorts; and 4 in the 8 mg cohort. The mean time to onset of an initial gout flare was 13.6 d (range 2-32 d). No relationship was observed between PEG-uricase dose and the time to an initial gout flare. Non-steroidal anti-inflammatory drugs, colchicine, or oral corticosteroids were used as prophylaxis or treatment for gout flares in 23/24 subjects.

The invention has been described in terms of preferred embodiments thereof, but is more broadly applicable as will be understood by those skilled in the art. The scope of the invention is only limited by the following claims.

What is claimed is:

1. A method for lowering elevated uric acid levels in a patient comprising administering to said patient an intravenous injection of PEG-uricase having a dosage from about 4 to about 12 mg of uricase, the uricase consisting of the amino acid sequence of SEQ ID NO:8, wherein said administration takes place from about every 2 to 4 weeks, wherein a plasma uricase activity level is undetectable in the patient prior to a first intravenous injection of PEG-uricase, and wherein the plasma uricase activity level is detectable about 21 days after the intravenous injection.

2. The method of claim 1, wherein said dosage is between 4 and 8 mg of uricase.

3. The method of claim 1, wherein said dosage is between 8 and 12 mg of uricase.

4. The method of claim 1, wherein said dosage is about 4 mg of uricase.

5. The method of claim 1, wherein said patient is suffering from gout.

6. The method of claim 5, wherein said gout is refractory.

7. The method of claim 5, wherein said gout is chronic or tophaceous.

8. The method of claim 1, wherein said patient has a plasma level of uric acid (pUAc) of more than about 6 mg/dL before said administration.

9. The method of claim 1, wherein the plasma uricase activity level is detectable in the patient from about 26 mU/mL to about 6.5 mU/mL about 21 days after the intravenous injection.

10. A method for lowering elevated uric acid levels in a patient comprising administering to said patient an intravenous injection of PEG-uricase having a dosage from about 0.5 to about 12 mg of uricase, the uricase consisting of the amino acid sequence of SEQ ID NO:8, wherein said administration takes place from about every 2 to 4 weeks, and wherein a plasma uricase activity level is undetectable in the patient prior to a first intravenous injection of PEG-uricase, and wherein the plasma uricase activity level is detectable about 21 days after the intravenous injection.

11. The method of claim 10, wherein said dosage is between 4 and 8 mg of uricase.

12. The method of claim 10, wherein said dosage is between 8 and 12 mg of uricase.

13. The method of claim 10, wherein said dosage is about 4 mg of uricase.

14. The method of claim 10, wherein said patient is suffering from gout.

15. The method of claim 14, wherein said gout is refractory.

16. The method of claim 14, wherein said gout is chronic or tophaceous.

17. The method of claim 10, wherein said patient has a plasma level of uric acid (pUAc) of more than about 6 mg/dL before said administration.

18. The method of claim 10, wherein the plasma uricase activity level is detectable in the patient from about 26 mU/mL to about 6.5 mU/mL about 21 days after the intravenous injection.

* * * * *

SEQUENCE LISTING

<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Pig Liver Uricase (sense)

<400> SEQUENCE: 1
gcgcgaattc catggctcat taccgtaatg actaca                               36

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Pig Liver Uricase (antisense)

<400> SEQUENCE: 2
gcgctctaga agcttccatg gtcacagcct tgaagtcagc                           40

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Baboon (D3H) Liver Uricase (sense)

<400> SEQUENCE: 3
gcgcgaattc catggcccac taccataaca actat                                35

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Baboon (D3H) Liver Uricase (antisense)

<400> SEQUENCE: 4
gcgcccatgg tctagatcac agtcttgaag acaacttcct                           40

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PBC-DeltaNC Uricase (sense)

<400> SEQUENCE: 5
gcgcatatga cttacaaaaa gaatgatgag gtagag                               36

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PBC-DeltaNC Uricase (antisense)

<400> SEQUENCE: 6
ccgtctagat taagacaact tcctcttgac tgtaccagta attttccgt atgg          54

<210> SEQ ID NO 7
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Pig-KS-DeltaN

<400> SEQUENCE: 7

Met Thr Tyr Lys Lys Asn Asp Glu Val Glu Phe Val Arg Thr Gly Tyr
1               5                   10                  15

Gly Lys Asp Met Ile Lys Val Leu His Ile Gln Arg Asp Gly Lys Tyr
            20                  25                  30

His Ser Ile Lys Glu Val Ala Thr Thr Val Gln Leu Thr Leu Ser Ser
        35                  40                  45

Lys Lys Asp Tyr Leu His Gly Asp Asn Ser Asp Val Ile Pro Thr Asp
    50                  55                  60

Thr Ile Lys Asn Thr Val Asn Val Leu Ala Lys Phe Lys Gly Ile Lys
65                  70                  75                  80

Ser Ile Glu Thr Phe Ala Val Thr Ile Cys Glu His Phe Leu Ser Ser
                85                  90                  95

Phe Lys His Val Ile Arg Ala Gln Val Tyr Val Glu Glu Val Pro Trp
            100                 105                 110

Lys Arg Phe Glu Lys Asn Gly Val Lys His Val His Ala Phe Ile Tyr
        115                 120                 125

Thr Pro Thr Gly Thr His Phe Cys Glu Val Glu Gln Ile Arg Asn Gly
    130                 135                 140

Pro Pro Val Ile His Ser Gly Ile Lys Asp Leu Lys Val Leu Lys Thr
145                 150                 155                 160

Thr Gln Ser Gly Phe Glu Gly Phe Ile Lys Asp Gln Phe Thr Thr Leu
                165                 170                 175

Pro Glu Val Lys Asp Arg Cys Phe Ala Thr Gln Val Tyr Cys Lys Trp
            180                 185                 190

Arg Tyr His Gln Gly Arg Asp Val Asp Phe Glu Ala Thr Trp Asp Thr
        195                 200                 205

Val Arg Ser Ile Val Leu Gln Lys Phe Ala Gly Pro Tyr Asp Lys Gly
    210                 215                 220

Glu Tyr Ser Pro Ser Val Gln Lys Thr Leu Tyr Asp Ile Gln Val Leu
225                 230                 235                 240

Thr Leu Gly Gln Val Pro Glu Ile Glu Asp Met Glu Ile Ser Leu Pro
                245                 250                 255

Asn Ile His Tyr Leu Asn Ile Asp Met Ser Lys Met Gly Leu Ile Asn
            260                 265                 270

```
Lys Glu Glu Val Leu Leu Pro Leu Asp Asn Pro Tyr Gly Lys Ile Thr
            275                 280                 285

Gly Thr Val Lys Arg Lys Leu Ser Ser Arg Leu
    290                 295

<210> SEQ ID NO 8
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Pig-KS-DeltaN without starting Met

<400> SEQUENCE: 8

Thr Tyr Lys Lys Asn Asp Glu Val Glu Phe Val Arg Thr Gly Tyr Gly
1               5                   10                  15

Lys Asp Met Ile Lys Val Leu His Ile Gln Arg Asp Gly Lys Tyr His
            20                  25                  30

Ser Ile Lys Glu Val Ala Thr Thr Val Gln Leu Thr Leu Ser Ser Lys
        35                  40                  45

Lys Asp Tyr Leu His Gly Asp Asn Ser Asp Val Ile Pro Thr Asp Thr
    50                  55                  60

Ile Lys Asn Thr Val Asn Val Leu Ala Lys Phe Lys Gly Ile Lys Ser
65                  70                  75                  80

Ile Glu Thr Phe Ala Val Thr Ile Cys Glu His Phe Leu Ser Ser Phe
                85                  90                  95

Lys His Val Ile Arg Ala Gln Val Tyr Val Glu Glu Val Pro Trp Lys
            100                 105                 110

Arg Phe Glu Lys Asn Gly Val Lys His Val His Ala Phe Ile Tyr Thr
        115                 120                 125

Pro Thr Gly Thr His Phe Cys Glu Val Glu Gln Ile Arg Asn Gly Pro
    130                 135                 140

Pro Val Ile His Ser Gly Ile Lys Asp Leu Lys Val Leu Lys Thr Thr
145                 150                 155                 160

Gln Ser Gly Phe Glu Gly Phe Ile Lys Asp Gln Phe Thr Thr Leu Pro
                165                 170                 175

Glu Val Lys Asp Arg Cys Phe Ala Thr Gln Val Tyr Cys Lys Trp Arg
            180                 185                 190

Tyr His Gln Gly Arg Asp Val Asp Phe Glu Ala Thr Trp Asp Thr Val
        195                 200                 205

Arg Ser Ile Val Leu Gln Lys Phe Ala Gly Pro Tyr Asp Lys Gly Glu
    210                 215                 220

Tyr Ser Pro Ser Val Gln Lys Thr Leu Tyr Asp Ile Gln Val Leu Thr
225                 230                 235                 240

Leu Gly Gln Val Pro Glu Ile Glu Asp Met Glu Ile Ser Leu Pro Asn
                245                 250                 255

Ile His Tyr Leu Asn Ile Asp Met Ser Lys Met Gly Leu Ile Asn Lys
            260                 265                 270

Glu Glu Val Leu Leu Pro Leu Asp Asn Pro Tyr Gly Lys Ile Thr Gly
        275                 280                 285

Thr Val Lys Arg Lys Leu Ser Ser Arg Leu
    290                 295
```

<210> SEQ ID NO 9
<211> LENGTH: 897
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Pig-KS-DeltaNA

<400> SEQUENCE: 9

```
atgacttaca aaagaatga tgaggtagag tttgtccgaa ctggctatgg gaaggatatg      60
ataaaagttc tccatattca gcgagatgga aaatatcaca gcattaaaga ggtggcaact    120
acagtgcaac tgactttgag ctccaaaaaa gattacctgc atggagacaa ttcagatgtc    180
atccctacag acaccatcaa gaacacagtt aatgtcctgg cgaagttcaa aggcatcaaa    240
agcatagaaa cttttgctgt gactatctgt gagcatttcc tttcttcctt caagcatgtc    300
atcagagctc aagtctatgt ggaagaagtt ccttggaagc gttttgaaaa gaatggagtt    360
aagcatgtcc atgcatttat ttatactcct actggaacgc acttctgtga ggttgaacag    420
ataaggaatg gacctccagt cattcattct ggaatcaaag acctaaaagt cttgaaaaca    480
acccagtctg gctttgaagg attcatcaag gaccagttca ccaccctccc tgaggtgaag    540
gaccggtgct tgccacccca gtgtactgca aatggcgct  accaccaggg cagagatgtg    600
gactttgagg ccacctggga cactgttagg agcattgtcc tgcagaaatt tgctgggccc    660
tatgacaaag gcgagtactc gccctctgtc cagaagacac tctatgacat ccaggtgctc    720
accctgggcc aggttcctga gataagagat atggaaatca gcctgccaaa tattcactac    780
ttaaacatag acatgtccaa aatgggactg atcaacaagg aagaggtctt gctaccttta    840
gacaatccat atggaaaaat tactggtaca gtcaagagga gttgtcttc aagactg       897
```

<210> SEQ ID NO 10
<211> LENGTH: 894
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Pig-KS-DeltaN without starting ATG

<400> SEQUENCE: 10

```
acttacaaaa agaatgatga ggtagagttt gtccgaactg gctatgggaa ggatatgata      60
aaagttctcc atattcagcg agatggaaaa tatcacagca ttaagaggt ggcaactaca    120 gtgcaactga ctttgagctc aaaaaagat tacctgcatg gagacaattc agatgtcatc    180
cctacagaca ccatcaagaa cacagttaat gtcctggcga agttcaaagg catcaaaagc    240
atagaaactt ttgctgtgac tatctgtgag catttccttt cttccttcaa gcatgtcatc    300
agagctcaag tctatgtgga agaagttcct tggaagcgtt tgaaaagaa tggagttaag    360 catgtccatg catttattta tactcctact ggaacgcact tctgtgaggt tgaacagata    420
aggaatggac ctccagtcat tcattctgga atcaaagacc taaaagtctt gaaaacaacc    480
cagtctggct ttgaaggatt catcaaggac cagttcacca ccctccctga ggtgaaggac    540
cggtgctttg ccacccaagt gtactgcaaa tggcgctacc accagggcag agatgtggac    600
tttgaggcca cctgggacac tgttaggagc attgtcctgc agaaatttgc tgggccctat    660
gacaaaggcg agtactcgcc ctctgtccag aagacactct atgacatcca ggtgctcacc    720
ctgggccagg ttcctgagat agaagatatg gaaatcagcc tgccaaatat tcactactta    780
```

```
aacatagaca tgtccaaaat gggactgatc aacaaggaag aggtcttgct acctttagac    840
aatccatatg gaaaaattac tggtacagtc aagaggaagt tgtcttcaag actg          894
```

<210> SEQ ID NO 11
<211> LENGTH: 304
<212> TYPE: PRT
<213> ORGANISM: Sus scrofa

<400> SEQUENCE: 11

```
Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Arg Ile Thr Gly Thr Val Lys Arg Lys Leu Thr Ser Arg Leu
    290                 295                 300
```

<210> SEQ ID NO 12
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PBC-DeltaNC

```
<400> SEQUENCE: 12

Met Thr Tyr Lys Lys Asn Asp Glu Val Glu Phe Val Arg Thr Gly Tyr
1               5                   10                  15

Gly Lys Asp Met Ile Lys Val Leu His Ile Gln Arg Asp Gly Lys Tyr
                20                  25                  30

His Ser Ile Lys Glu Val Ala Thr Thr Val Gln Leu Thr Leu Ser Ser
            35                  40                  45

Lys Lys Asp Tyr Leu His Gly Asp Asn Ser Asp Val Ile Pro Thr Asp
        50                  55                  60

Thr Ile Lys Asn Thr Val Asn Val Leu Ala Lys Phe Lys Gly Ile Lys
65                  70                  75                  80

Ser Ile Glu Thr Phe Ala Val Thr Ile Cys Glu His Phe Leu Ser Ser
                85                  90                  95

Phe Lys His Val Ile Arg Ala Gln Val Tyr Val Glu Val Pro Trp
                100                 105                 110

Lys Arg Phe Glu Lys Asn Gly Val Lys His Val His Ala Phe Ile Tyr
                115                 120                 125

Thr Pro Thr Gly Thr His Phe Cys Glu Val Gln Ile Arg Asn Gly
        130                 135                 140

Pro Pro Val Ile His Ser Gly Ile Lys Asp Leu Lys Val Leu Lys Thr
145                 150                 155                 160

Thr Gln Ser Gly Phe Glu Gly Phe Ile Lys Asp Gln Phe Thr Thr Leu
                165                 170                 175

Pro Glu Val Lys Asp Arg Cys Phe Ala Thr Gln Val Tyr Cys Lys Trp
                180                 185                 190

Arg Tyr His Gln Gly Arg Asp Val Asp Phe Glu Ala Thr Trp Asp Thr
                195                 200                 205

Val Arg Ser Ile Val Leu Gln Lys Phe Ala Gly Pro Tyr Asp Lys Gly
210                 215                 220

Glu Tyr Ser Pro Ser Val Gln Lys Thr Leu Tyr Asp Ile Gln Val Leu
225                 230                 235                 240

Ser Leu Ser Arg Val Pro Glu Ile Glu Asp Met Glu Ile Ser Leu Pro
                245                 250                 255

Asn Ile His Tyr Phe Asn Ile Asp Met Ser Lys Met Gly Leu Ile Asn
                260                 265                 270

Lys Glu Glu Val Leu Leu Pro Leu Asp Asn Pro Tyr Gly Lys Ile Thr
                275                 280                 285

Gly Thr Val Lys Arg Lys Leu Ser
        290                 295

<210> SEQ ID NO 13
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PBC-DeltaNC without starting Met

<400> SEQUENCE: 13

Thr Tyr Lys Lys Asn Asp Glu Val Glu Phe Val Arg Thr Gly Tyr Gly
1               5                   10                  15

Lys Asp Met Ile Lys Val Leu His Ile Gln Arg Asp Gly Lys Tyr His
                20                  25                  30

Ser Ile Lys Glu Val Ala Thr Thr Val Gln Leu Thr Leu Ser Ser Lys
            35                  40                  45
```

```
Lys Asp Tyr Leu His Gly Asp Asn Ser Asp Val Ile Pro Thr Asp Thr
 50                  55                  60
Ile Lys Asn Thr Val Asn Val Leu Ala Lys Phe Lys Gly Ile Lys Ser
 65                  70                  75                  80
Ile Glu Thr Phe Ala Val Thr Ile Cys Glu His Phe Leu Ser Ser Phe
                 85                  90                  95
Lys His Val Ile Arg Ala Gln Val Tyr Val Glu Glu Val Pro Trp Lys
            100                 105                 110
Arg Phe Glu Lys Asn Gly Val Lys His Val His Ala Phe Ile Tyr Thr
        115                 120                 125
Pro Thr Gly Thr His Phe Cys Glu Val Glu Gln Ile Arg Asn Gly Pro
    130                 135                 140
Pro Val Ile His Ser Gly Ile Lys Asp Leu Lys Val Leu Lys Thr Thr
145                 150                 155                 160
Gln Ser Gly Phe Glu Gly Phe Ile Lys Asp Gln Phe Thr Thr Leu Pro
                165                 170                 175
Glu Val Lys Asp Arg Cys Phe Ala Thr Gln Val Tyr Cys Lys Trp Arg
            180                 185                 190
Tyr His Gln Gly Arg Asp Val Asp Phe Glu Ala Thr Trp Asp Thr Val
        195                 200                 205
Arg Ser Ile Val Leu Gln Lys Phe Ala Gly Pro Tyr Asp Lys Gly Glu
    210                 215                 220
Tyr Ser Pro Ser Val Gln Lys Thr Leu Tyr Asp Ile Gln Val Leu Ser
225                 230                 235                 240
Leu Ser Arg Val Pro Glu Ile Glu Asp Met Gly Ile Ser Leu Pro Asn
                245                 250                 255
Ile His Tyr Phe Asn Ile Asp Met Ser Lys Met Gly Leu Ile Asn Lys
            260                 265                 270
Glu Glu Val Leu Leu Pro Leu Asp Asn Pro Tyr Gly Lys Ile Thr Gly
        275                 280                 285
Thr Val Lys Arg Lys Leu Ser
    290                 295

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PBC-DeltaNC (Fragment 44-56 of PBC-DeltaNC)

<400> SEQUENCE: 14

Ala Thr Thr Val Gln Leu Thr Leu Ser Ser Lys Lys Asp
 1               5                  10

<210> SEQ ID NO 15
<211> LENGTH: 936
<212> TYPE: DNA
<213> ORGANISM: Papio hamadryas

<400> SEQUENCE: 15
ccagaagaaa atggccgact accataacaa ctataaaaag aatgatgaat tggagtttgt      60
ccgaactggc tatgggaagg atatggtaaa agttctccat attcagcgag atggaaaata     120
tcacagcatt aaagaggtgg caacttcagt gcaacttact ctgagttcca aaaaagatta     180
cctgcatgga gataattcag atatcatccc tacagacacc atcaagaaca cagttcatgt     240
```

```
cttggcaaag tttaagggaa tcaaaagcat agaagccttt ggtgtgaata tttgtgagta    300
ttttctttct tcttttaacc atgtaatccg agctcaagtc tacgtggaag aaatcccttg    360
gaagcgtctt gaaaagaatg gagttaagca tgtccatgca tttattcaca ctcccactgg    420
aacacacttc tgtgaagttg aacaactgag aagtggaccc cccgtcatta cttctggaat    480
caaagacctc aaggtcttga aacaacaca gtctggattt gaaggtttca tcaaggacca     540
gttcaccacc ctccctgagg tgaaggaccg atgctttgcc acccaagtgt actgcaagtg    600
gcgctaccac cagtgcaggg atgtggactt cgaggctacc tggggcacca ttcgggacct    660
tgtcctggag aaatttgctg ggccctatga caaaggcgag tactcaccct ctgtgcagaa    720
gaccctctat gatatccagg tgctctccct gagccgagtt cctgagatag aagatatgga    780
aatcagcctg ccaaacattc actacttcaa tatagacatg tccaaaatgg gtctgatcaa    840
caaggaagag gtcttgctgc cattagacaa tccatatgga aaaattactg gtacagtcaa    900
gaggaagttg tcttcaagac tgtgacattg tggcca                             936
```

<210> SEQ ID NO 16
<211> LENGTH: 304
<212> TYPE: PRT
<213> ORGANISM: Papio hamadryas

<400> SEQUENCE: 16

```
Met Ala Asp Tyr His Asn Asn Tyr Lys Lys Asn Asp Glu Leu Glu Phe
  1               5                  10                  15

Val Arg Thr Gly Tyr Gly Lys Asp Met Val Lys Val Leu His Ile Gln
             20                  25                  30

Arg Asp Gly Lys Tyr His Ser Ile Lys Glu Val Ala Thr Ser Val Gln
         35                  40                  45

Leu Thr Leu Ser Ser Lys Lys Asp Tyr Leu His Gly Asp Asn Ser Asp
     50                  55                  60

Ile Ile Pro Thr Asp Thr Ile Lys Asn Thr Val His Val Leu Ala Lys
 65                  70                  75                  80

Phe Lys Gly Ile Lys Ser Ile Glu Ala Phe Gly Val Asn Ile Cys Glu
                 85                  90                  95

Tyr Phe Leu Ser Ser Phe Asn His Val Ile Arg Ala Gln Val Tyr Val
            100                 105                 110

Glu Glu Ile Pro Trp Lys Arg Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Pro Val Ile Thr Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Gly Thr Ile Arg Asp Leu Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255
```

```
Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300
```